(12) United States Patent
Aunger et al.

(10) Patent No.: US 11,328,088 B2
(45) Date of Patent: *May 10, 2022

(54) TRUST BASED ACCESS TO RECORDS VIA ENCRYPTED PROTOCOL COMMUNICATIONS WITH AUTHENTICATION SYSTEM

(71) Applicant: Akiri, Inc., Foster City, CA (US)

(72) Inventors: Charles Aunger, Hayward, CA (US); Adriaan Ligtenberg, Amsterdam (NL); Tom Frederick, Menlo Park, CA (US); Jack Stockert, Los Altos, CA (US); Doug Given, Menlo Park, CA (US); Ketan Paranjape, Portland, OR (US); Bernard Mangold, Mercer Island, WA (US); Michael Hodgkins, San Diego, CA (US); Warren Templeton, San Francisco, CA (US)

(73) Assignee: Akiri, Inc., Foster City, CA (US)

( * ) Notice: Subject to any disclaimer, the term of this patent is extended or adjusted under 35 U.S.C. 154(b) by 155 days.

This patent is subject to a terminal disclaimer.

(21) Appl. No.: 16/360,338

(22) Filed: Mar. 21, 2019

(65) Prior Publication Data

US 2020/0057867 A1 Feb. 20, 2020

Related U.S. Application Data

(63) Continuation of application No. 15/877,828, filed on Jan. 23, 2018, now Pat. No. 10,255,458.

(Continued)

(51) Int. Cl.
*G06F 21/62* (2013.01)
*G06F 21/60* (2013.01)
(Continued)

(52) U.S. Cl.
CPC ........ *G06F 21/6245* (2013.01); *G06F 21/602* (2013.01); *G06F 21/6263* (2013.01);
(Continued)

(58) Field of Classification Search
CPC ............. G06F 21/6245; G06F 21/6263; H04L 63/083; H04L 63/168; H04L 63/0442; H04L 63/0428; H04L 63/102; G16H 10/60
See application file for complete search history.

(56) References Cited

U.S. PATENT DOCUMENTS 6,988,075 B1  1/2006 Hacker
7,698,154 B2  4/2010 Marchosky
(Continued)

OTHER PUBLICATIONS

International Search Report and Written Opinion for International Application No. PCT/US2018/014894 dated Apr. 20, 2018, in 18 pages.

(Continued)

*Primary Examiner* — Khoi V Le
(74) *Attorney, Agent, or Firm* — Knobbe, Martens, Olson & Bear, LLP

(57) ABSTRACT

Systems and techniques are disclosed for trust based access to records via encrypted protocol communications with an authentication system. An example system is configured to authorize and provide selective and secured access to sensitive medical information according to one or more trusted relationships. The system is configured to receive a request for access to a patient's health record from an outside entity. Authentication information associated with the outside entity is determined. Whether the outside entity is authorized to access the requested data is determined. The determination is based on existence of a trust relationship being established between the outside entity and the patient, the trust relationship established by an action of the patient or a (Continued)

patient's representative. Access to the patient's health record is enabled based on a positive determination.

18 Claims, 16 Drawing Sheets

Related U.S. Application Data

(60) Provisional application No. 62/510,160, filed on May 23, 2017, provisional application No. 62/460,341, filed on Feb. 17, 2017, provisional application No. 62/449,204, filed on Jan. 23, 2017.

(51) Int. Cl.
*G16H 10/60* (2018.01)
*H04L 29/06* (2006.01)

(52) U.S. Cl.
CPC ......... *G16H 10/60* (2018.01); *H04L 63/0428* (2013.01); *H04L 63/083* (2013.01); *H04L 63/102* (2013.01); *H04L 63/166* (2013.01); *H04L 63/168* (2013.01); *H04L 63/0442* (2013.01)

(56) References Cited

U.S. PATENT DOCUMENTS

| | | | |
|---|---|---|---|
| 7,979,569 B2 | 7/2011 | Eisner et al. | |
| 7,983,934 B1* | 7/2011 | Sholtis | G16H 40/67 705/2 |
| 8,024,581 B2 | 9/2011 | Spalka et al. | |
| 8,108,311 B2 | 1/2012 | Herlitz | |
| 8,260,709 B2 | 9/2012 | Holla et al. | |
| 8,516,267 B2 | 8/2013 | Spalka et al. | |
| 8,600,895 B2 | 12/2013 | Felsher | |
| 8,661,247 B2 | 2/2014 | Spalka et al. | |
| 8,695,106 B2 | 4/2014 | Spalka et al. | |
| 8,699,705 B2 | 4/2014 | Spalka et al. | |
| 8,738,396 B2 | 5/2014 | Green, III et al. | |
| 8,924,236 B2 | 12/2014 | Marchosky | |
| 8,959,027 B2 | 2/2015 | Kusens | |
| 9,053,338 B2 | 6/2015 | Baker | |
| 9,141,726 B1 | 9/2015 | Mcnair | |
| 9,141,822 B2 | 9/2015 | Lehnhardt et al. | |
| 9,195,802 B2 | 11/2015 | Henderson et al. | |
| 9,213,812 B1 | 12/2015 | Windell et al. | |
| 9,235,725 B2 | 1/2016 | Spalka et al. | |
| 9,330,236 B2 | 5/2016 | Kusens | |
| 9,459,843 B1 | 10/2016 | Smith et al. | |
| 10,255,458 B2 | 4/2019 | Aunger et al. | |
| 2007/0078687 A1* | 4/2007 | Dettinger | G06Q 20/40 705/3 |
| 2008/0306872 A1* | 12/2008 | Felsher | G06Q 20/367 705/51 |
| 2013/0006865 A1* | 1/2013 | Spates | H04L 63/062 705/50 |
| 2015/0046192 A1 | 2/2015 | Raduchel | |
| 2015/0213195 A1* | 7/2015 | Blechman | G16H 10/60 705/51 |
| 2017/0091397 A1 | 3/2017 | Shah | |
| 2017/0161439 A1 | 6/2017 | Raduchel et al. | |
| 2017/0364637 A1 | 12/2017 | Kshepakaran et al. | |
| 2018/0211058 A1 | 7/2018 | Aunger et al. | |
| 2018/0211059 A1 | 7/2018 | Aunger et al. | |

OTHER PUBLICATIONS

International Search Report and Written Opinion for International Application No. PCT/US2018/014896 dated May 7, 2018, in 19 pages.

* cited by examiner

FIG. 11

TRUST BASED ACCESS TO RECORDS VIA ENCRYPTED PROTOCOL COMMUNICATIONS WITH AUTHENTICATION SYSTEM

CROSS-REFERENCE TO RELATED APPLICATIONS

This application is a continuation of, and claims priority to, U.S. patent application Ser. No. 15/877,828, titled "TRUST BASED ACCESS TO RECORDS VIA ENCRYPTED PROTOCOL COMMUNICATIONS WITH AUTHENTICATION SYSTEM" and filed on Jan. 23, 2018. U.S. patent application Ser. No. 15/877,828 is hereby incorporated by reference in its entirety.

Any and all applications for which a foreign or domestic priority claim is identified in the Application Data Sheet as filed with the present application are hereby incorporated by reference in their entirety under 37 CFR 1.57.

BACKGROUND

Patient health records are invaluable in determining a patient's current health state and future health risk indicators. Medical information and associated records, however, are generated using complex disparate proprietary systems and stored in different locations making it difficult to access and compile. Existing systems also often provide inconsistent access to stored medical information. For example, a hospital may have many different proprietary computer systems that each separately record and maintain medical information of patients in unique proprietary formats. A medical professional can access the medical information, but only on specific computer systems in specific wards of the hospital. This often results in requests for hard copies of medical information pulled one at a time from various storage systems by a variety of personnel, causing significant wait times.

Privacy concerns and HIPAA regulations further complicate a medical professional's ability to transfer and review medical information. In existing systems, patients are often unaware of where their medical information is stored, who has access to it, how to obtain copies of it, how to provide copies to other medical professionals or how to ensure privacy of the medical information. Existing systems do not provide a full and/or consistent accounting of the use of medical information. For example, existing systems cannot indicate who accessed medical information, when the information was accessed or where it was accessed.

SUMMARY

Particular embodiments of the subject matter described in this specification can be implemented so as to realize one or more of the following advantages. Utilizing a system described below, electronic health records of patients can be collected across a broad spectrum of care providers and can be maintained by the system in a secure, appropriately available, and traceable record. The present disclosure provides tight control for access to health records of each patient. This control can, for example, be based on express permissions conveniently and securely obtained directly from the patient. The present disclosure also provides a system that stores health records as chunks or portions of data for each patient that can be separately accessible. For example, each chunk can be referenced by an anonymized identifier associated with the patient to increase privacy protections for the patient. The present disclosure also provides a system in which outside entities, such as medical professionals, can be individually authorized and provided access to only specific portions of a patient's health record. Furthermore, through a unique application-layer protocol, access to a patient's health record by an outside entity can be restricted such that the outside entity is required to view the accessed information on specific user devices, at specific times, or with other similar requirements. In this way, patients can have complete control over their health records, and can easily (1) authorize selected outside entities access to specified portions of their health records, or (2) de-authorize access, for example upon switching doctors, hospitals, care providers, and so on.

As will be described below, the system can allow patients to 'trust' particular outside entities and thereby provide access to specific portions (or the entirety) of the patient's medical records and history. As referred to in the present specification, an outside entity can be any person, care provider, insurance company, practice group, hospital, medical professional, medical researcher, or other entity. For example, a patient can walk into a new doctor's office, and via use of a user device operating a software application, can indicate that he/she authorizes the new doctor's access to his/her health records. Furthermore, the patient can indicate select portions (or all portions) of medical information that the new doctor is able to access. As an example, a podiatrist may be given access to a first portion of medical information but be restricted from accessing remaining portions. In this example, the podiatrist may access general medical information, such as medication allergies; podiatry information, such as information from prior podiatrists of the patient; but not other medical information that is unrelated to the podiatrist's care. In this way, access to health records stored by the system can be limited to trusted entities and for specific purposes.

In addition to enforcing access restrictions to health records on the system, user devices utilized by outside entities can further enforce privacy restrictions. For example, user devices can be required to execute a particular application to access health records. In this example, an 'app' can be downloaded from an electronic application store, a web application accessed via a browser, and so on. Different applications may be associated with disparate functionality, and the user devices can execute one or more applications to perform specific functionality. As another example, the user device can include particular firmware, or execute a particular software agent, on the user device to provide low-level security. The user device can also access health records over a network that includes network components associated with or specifically trusted by the system. Through user device configurations and specified access requirements, access to received data can be controlled. That is, even if encrypted medical information is obtained from the system or the user device, particular user device requirements must be satisfied to unencrypt and/or view the medical information. As an example, a user device can request medical information associated with a particular patient, and upon receipt of the requested medical information from the system, an application executing on the user device can access (for example, by decryption) the medical information based on the requirements that a specified user is operating an authorized device. This can occur, for example, where a particular doctor has provided authentication information via the doctor's authorized device, and the particular doctor has been trusted to view the medical information. Other access requirements can include, for example, whether an access time of the information is within an allowed time period or whether the user device is authorized to present the medical information. An authorized user device is a device that a particular user is known to use. Alternatively, an authorized user device is a specific device appropriate for the medical information, such as user devices configured to view Digital Imaging and Communications in Medicine 'DICOM' image information.

To ensure the safe transfer of information from the system to user devices, a particular protocol can be utilized to enable encrypted communications. The protocol can be, for example, an application layer protocol transmitted over TCP, UDP, and so on (herein referred to as 'health communication protocol'). The protocol can enable a receiving user device to ensure that it is properly authorized to present the medical information. Additionally, the protocol can allow networks, user devices, and so on, to rapidly identify network traffic (for example, packets) as being medical information. For example, a particular port can optionally be assigned for use by the application layer protocol.

The techniques described in this specification address problems arising specifically from electronic medical records and provide solutions for the improvement of electronic medical records. For example, in current systems, medical information is generated mainly for billing purposes. That is, the medical professional records his/her notes, findings, and so on while referencing or including medical images, for purposes of triggering payment of fees in various required insurance databases and at different levels of specificity. But the information is not necessarily recorded for purposes of creating a patient health history. This recorded information is therefore utilized for disparate purposes, and no central 'longitudinal' record may exist for a patient. Rather the recorded information is separately recorded according to billing needs on disparate, non-compatible systems. In contrast, the system described herein enables medical professionals to record medical information divorced from such restrictions, thus providing for a true longitudinal record of the patient.

Additionally, given the sensitive nature of medical information, the system ensures that medical information is only viewable or accessible by medical professionals who can easily be authorized and de-authorized by patients. The system can also ensure that medical professionals are provided access only to medical information for which they have a need. The system can further ensure that medical information is maintained by the system to reduce a possibility of the medical information being improperly accessed. As an example, with respect to reducing the possibility of unauthorized access, the system can associate an anonymized identifier with each patient. Medical information of each patient can reference the anonymized identifier while not referencing personally identifiable information of the patient. The system can determine access rights to medical information of a patient based on the associated identifier, such that even with improper access to the system, an attacker of the system would be unable to obtain and/or view medical information for specific patients. As will be described, an anonymized identifier associated with each patient can be generated based on features of the patient that uniquely describe the patient. Example features can include specific facts, such as a particular bone the patient broke at a particular age, a particular address at which the patient lived, a particular doctor the patient used to see, and so on. In this way, specific personally identifiable information, such as name, social security number, patient id number, and so on are not required, and may be specifically excluded as features. Based on the features, the system can generate an identifier for any subsequent information received about the patient and can associate the information with the identifier. The identifier can be, for example, a computed hash value (e.g., cryptographic hash) based on the features. In this way, medical information can be obfuscated, increasing privacy and security on an individual patient basis.

The details, including optional details, of one or more embodiments of the subject matter of this specification are set forth in the accompanying drawings and the description below. Other optional features, aspects, and advantages of the subject matter will become apparent from the description, the drawings, and the claims.

BRIEF DESCRIPTION OF THE DRAWINGS

The following drawings and the associated descriptions are provided to illustrate embodiments of the present disclosure and do not limit the scope of the claims. Aspects and many of the attendant advantages of this disclosure will become more readily appreciated as the same become better understood by reference to the following detailed description, when taken in conjunction with the accompanying drawings, wherein:

FIG. 11 includes example user interfaces presented on a user device.

DETAILED DESCRIPTION

Figure 1:
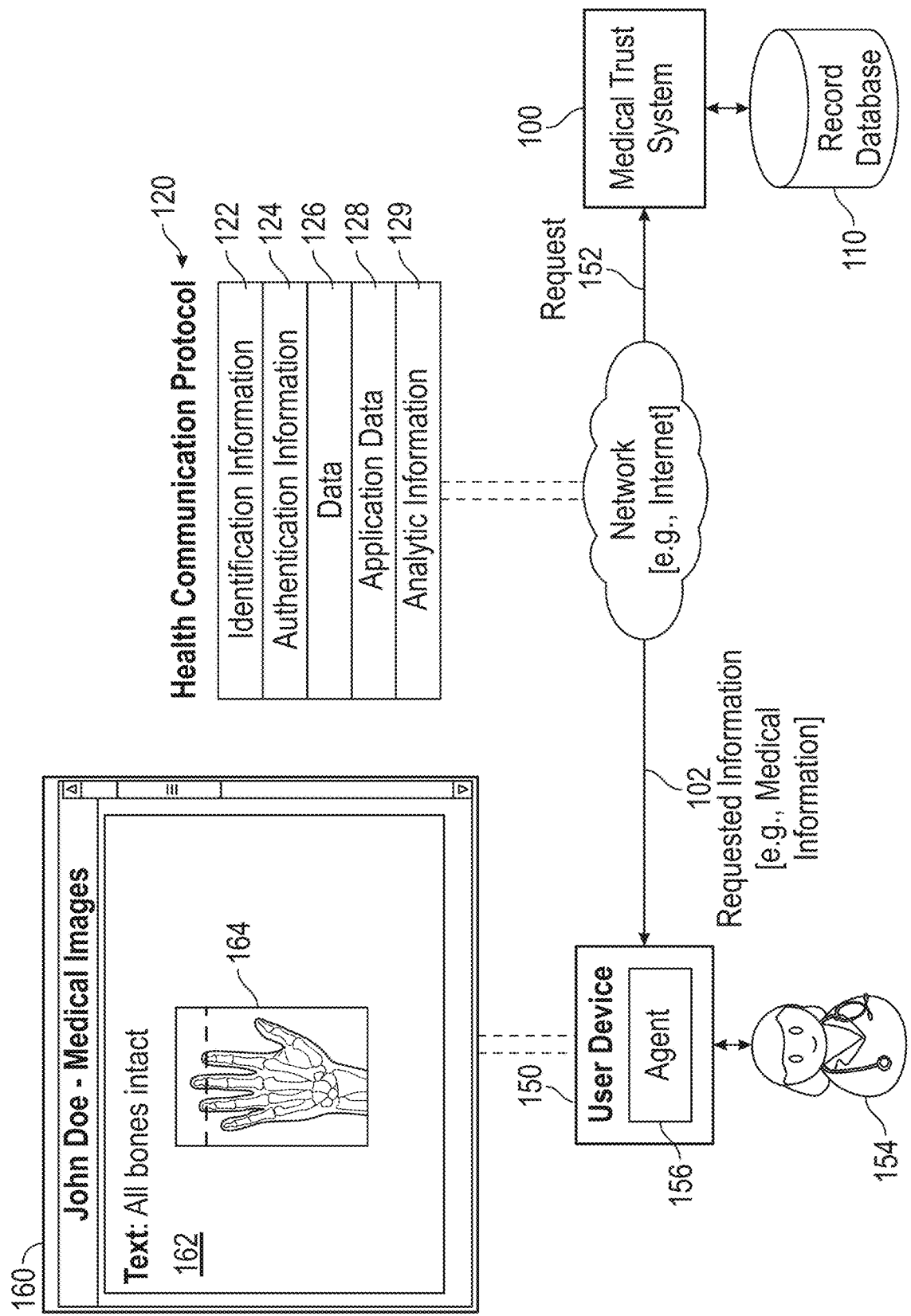
FIG. 1 illustrates access to an example health record maintained by an example medical trust system.

Although particular embodiments are described herein, other embodiments, including embodiments that do not provide all of the benefits and features set forth herein, will be apparent to those of ordinary skill in the art.

This specification describes a system that can maintain health records of patients while providing the patients with access controls to the maintained health records. A health record of a patient includes any medical information of the patient. Example medical information can include information recorded, generated, or determined, by medical professionals. Example medical information can further include information generated from medical systems, such as imaging systems, sensors, and so on. Example medical information can further include payment information, insurance information, and so on. Example medical information can further include biometric information associated with a patient. For example, information generated from smart devices, or wearable devices worn by a patient. The example information may include location data, heart rate data, facial identification information, EKG data, and so on. The system can optionally maintain the medical information as a plurality of portions of medical information. Optionally, and as will be described, metadata associated with each portion can be determined or stored, such that portions can be easily identifiable, for example by a search query. As will be described, each portion of information can represent a particular grouping of related medical information. Example groupings of medical information can include x-ray images, drug allergy information, blood tests, blood pressure, medical conditions, and so on.

The system can optionally implement a software-defined network that enables access to medical information stored via outside storage systems. The system can interface between user devices of patients or medical professionals and storage systems. For example, the system can authorize requests for information from patients or medical professions. The system can then route the requests via the software-defined network to the storage systems. The system can then route the requested information from the storage systems to the patients or medical professionals. Optionally, the system may not have access to the requested information. For example, the requested information may be encrypted and the system may route the encrypted information to intended recipients according to information included in packets being provided. The software-defined network may therefore enable access to medical information. Additionally, the software-defined network may therefore enable communication or connection between systems. For example, communication between a first system and a second system. The first system may be a user device of a patient or medical professional. The first system may further be a computer system or server system of a hospital, clinical researcher, and so on. The second system may be a storage system storing medical information. The second system may further be a user device of a patient or medical professional. The second system may further be a system associated with an insurance entity or clinical research entity aggregating medical information. The first system may request information from the second system or may provide information to the system (e.g., for storage). As will be described below, the system can ensure that access requests are authorized. For example, the authorization may be based on trust information.

The system can further ensure that a patient's health record is only accessible to particular medical professionals. In this specification, medical professionals, such as doctors or nurses, are referred to as outside entities. Outside entities can also include hospitals, practice groups, billing departments, insurance companies, and so on. Portions of a patient's health record can be separately trustable to outside entities that are indicated by the patient. A patient indicating 'trust' to, or 'trusting' an, outside entity represents the patient confirming that the outside entity can access at least a portion of his/her health record. Access to a health record, or a portion of a health record, indicates that the outside entity can perform one or more actions, including reading, writing, deleting, or otherwise modifying, the portion. For example, the patient can indicate that a first outside entity, such as a general practitioner, can access first portions of the health record. The patient can also indicate that a second outside entity, such as a pulmonologist, can access second portions of the health record. The system can store or otherwise maintain trust information associated with patients. For example, the system can store information indicating medical professionals authorized to access a patient's medical information, or specific portions of subsets of the patient's medical information.

The system can ensure that a patient's health record is only accessible at specific times. For example, the system can indicate a time period during which portions of the patient's health record are accessible. As will be described, the indicated time period can be specified in a response to a request for a portion of a patient's health record by an outside entity. A user device of the outside entity that receives the portion can be constrained to provide access to the portion during the time period. For a subsequent access to the portion, the outside entity can provide an additional request to the system. Examples of time period include work hours, work day, specific month, and so on.

The system can also ensure that a patient's health record is only accessible on specific user devices. For example, an outside entity can be required to utilize specific user devices located in his/her hospital or practice group. In this way, the outside entity may be unable to access a patient's health record on his/her personal mobile device. The system can further ensure that for particular received medical information, the user devices are appropriate to present the medical information. In this regard, the system can ensure that a tomography medical image is accessible only on user devices, such as computer systems, that include hardware or software required to access the medical image.

When indicating trust to an outside entity, a patient can specify portions of his/her health record that the outside entity can access. For example, and as will be described below with respect to FIG. 7B, the patient can utilize a user device, and can identify an outside entity to be trusted. Upon indicating trust to the outside entity, the patient can select portions of his/her health record that the outside entity can access. For example, the user device can present information indicating groupings of medical information, and optionally in consultation with the outside entity, the patient can select particular groupings to be trusted with the outside entity. Example groupings can include general medical information, particular types of medical images, allergies, health risks, general health history, physical limitations, or other relevant sub categories of patient information.

Furthermore, the system can determine portions of the health record that are to be trusted to the outside entity, for example based on information identifying an outside entity, and provide suggested authorization to the patient/user. The patient can subsequently view the determined portions, and confirm that the outside entity is authorized to access the suggested portions. As an example, if the outside entity is a podiatrist, the user device or system can suggest authorization to access information indicating portions that are generally utilized by podiatrists. The patient can then confirm that the specific portions are to be trusted to the podiatrist. The podiatrist can further request additional portions, for example based on a particular need, and the patient can confirm or deny trust to the additional portions. As patients and outside entities interact, and trust is indicated, the system can update portions of health records that outside entities commonly utilize. For example, the system can monitor indications of trust across many patients, and can determine, for example, that a podiatrist requests access to specific additional portions of a health record at a rate greater than a particular threshold rate. Similarly, the system can determine that a threshold quantity of podiatrists, such as 15% or 20% or 30%, request access to the specific additional portions at a rate greater than the particular threshold rate.

Outside entities can also be associated with trust policies that indicate portions of a health record each outside entity requires to properly provide care to patients. These trust policies can be generated for each medical professional, or optionally can be generated for a hospital, practice group, or healthcare provider. Medical professionals included in a hospital, practice group, or healthcare provider, can be assigned the same trust policies so that an organization can specify how patients interact with them. In this way, a patient can walk into a practice group and indicate trust to the practice group. As the patient sees doctors within the practice group, trust can be provided to the doctors automatically via the initial trust to the practice group. Additionally, as the patient sees doctors of differing types, trust can be provided to the doctors according to respective type. For example, a cardiologist can be trusted with first portions while a gastrologist can be trusted with second portions. In all cases in which trust is provided to a patient's health record, the patient can have the opportunity to review descriptions of the portions to be trusted, confirm that trust is to be provided and be alerted to trust being provided. For example, if the patient trusts the practice group, as each doctor accesses his/her medical record the patient can be notified.

While outside entities can be trusted with portions of a health record, access to the portions can be tightly constrained. For example, outside entities can be allowed to access the portions only at specific times and/or using specific user devices. For example, the system can maintain information identifying user devices known to be associated with an outside entity, and as will be described below, can constrain access to portions of the health record to the identified user devices. Examples of information identifying user devices include a MAC address, a UUID, a CPU serial number, and so on. Similarly, the outside entity can be provided with trust to portions of the health record for a particular amount of time. The particular amount of time can optionally be based on reasons the patient is seeing the outside entity or types of care being provided to the patient. As an example, the patient can discuss particular ailments with a doctor or nurse practitioner, for example at a walk-in clinic to receive fast care for common illnesses, and can indicate trust to the doctor or nurse practitioner to access his/her health record. The system can determine that trust is to be provided for a short amount of time, for example a single day, a few hours, and so on. Optionally, the user device operated by the patient can cause trust to the doctor or nurse practitioner to be de-authorized. Trust can be indicated to the doctor, nurse practitioner, at the start of an examination, and the user device can monitor location information (for example, global navigation satellite system 'GNSS' coordinates) of the user device. Based on the monitored location information, if the patient is determined to be leaving the walk-in clinic, the user device can automatically provide information to the system to de-authorize trust, or request confirmation from the patient to de-authorize trust.

To enforce such constraints, an application-layer protocol provided over, for example, TCP/UDP, can be utilized for communications between user devices and the system. As will be described below, with respect to FIG. 1, the application-layer protocol (herein referred to as a health communication protocol) can pass encrypted information from the system to user devices. To decrypt the information, one or more constraints or requirements may need to be satisfied. These constraints can be specified via the protocol. For example, a particular person may need to be logged into a user device, a particular user device may need to be utilized or a particular application may be required to view the received information. This foregoing list of constraints is not to be considered comprehensive or limiting, but is merely provided by way of example. Other constraints can be used as well.

User devices can be required to execute particular applications that can communicate with the system via the health communication protocol. To ensure security, a user device can be required to execute, or include, an application which receives information via the health communication protocol. Additionally, a user device can be required to include firmware on the user device, for example firmware that provides an additional authentication layer that can provide assurances that the user device corresponds to a known user device. A client component may also be required to be included on a network associated with an outside entity. For example, a local area network or a wide area network that connects user devices within a practice group or hospital. To increase a speed at which trusted medical information is available for access by outside entities, the system can cause user devices of the outside entities to be able to cache (for example, locally store) trusted medical information. The user devices can include particular user devices identified via the health communication protocol. For example, user devices known to be utilized by outside entities. The system can allow a user device of an outside entity to cache medical image information (for example, DICOM images) to reduce bandwidth requirements that would otherwise be required if access to the medical image information resulted in network calls to the system.

Outside entities can update portions of health records when they have been trusted. Outside entities can similarly generate additional portions for inclusion in health records. That is, an outside entity can access, edit, and/or include information in, trusted portions of a patient's health record. The system can monitor changes to the patient's health record, such that versions of the health record can be generated. A history of changes can be kept and previous versions of the history can be recalled. Optionally, the system can provide access to a version of the patient's health record for which the outside entity was trusted. As an example, if the patient de-authorizes trust with respect to the outside entity, any updates to the previously trusted portion can be inaccessible to the outside entity. However, and as will be described below with respect to FIG. 8, optionally the outside entity can retain access to the portions up until the patient de-authorized trust. In this way, the outside entity can have a record of the care provided to the patient. This record can, for example, provide indications that a particular duty of care was provided, or prove that care occurred for billing or insurance purposes. As will be described below, the outside entity can retain caches of trusted medical information and/or the system can provide a snapshot of the trusted medical information. A snapshot of trusted medical information can include medical information of a patient as it existed at a time when an outside entity was de-authorized.

Optionally, the patient can indicate that a particular outside entity is to be de-authorized, and also that access to the previously trusted medical information be revoked.

For example, a patient can trust a first podiatrist with portions of his/her health record, and the first podiatrist can record medical information in the health record. The patient can subsequently travel to a second podiatrist for a second opinion, and trust the second podiatrist with the same portions, including the first podiatrist's recorded medical information. The patient can then de-authorize trust to the second podiatrist, and return to the first podiatrist. The first podiatrist can then proceed with his/her initial recommendation, and at the patient's election, can be trusted with the information recorded by the second podiatrist to better inform the recommendation. That is, the patient can have complete autonomy over received medical information and can decide whether to inform the first podiatrist of the second opinion.

As described above, a user device operated by a patient can execute an application that can be utilized to indicate trust to outside entities. Additionally, and as will be described below with respect to FIG. 11, the application can enable access to the patient's health record, along with managing appointments for the patient, prescriptions, billing, and so on. For example, the patient can manage upcoming appointments. Similarly, outside entities, such as a front office of a practice group, can specify upcoming appointments of the patient. Optionally, the front office employees can be trusted with information identifying the patient's upcoming appointments and can include additional scheduled appointments which the patient can approve. The application can further provide information relevant to the patient's understanding of a doctor's diagnosis, such that the patient can better understand the diagnosis. As an example, the system, or application, can parse recorded information specified by the diagnosis and obtain relevant information based on the parsed information. For example, the system can identify usage of particular terms, such as cancer, and obtain information relevant to the particular terms.

Figure 11:
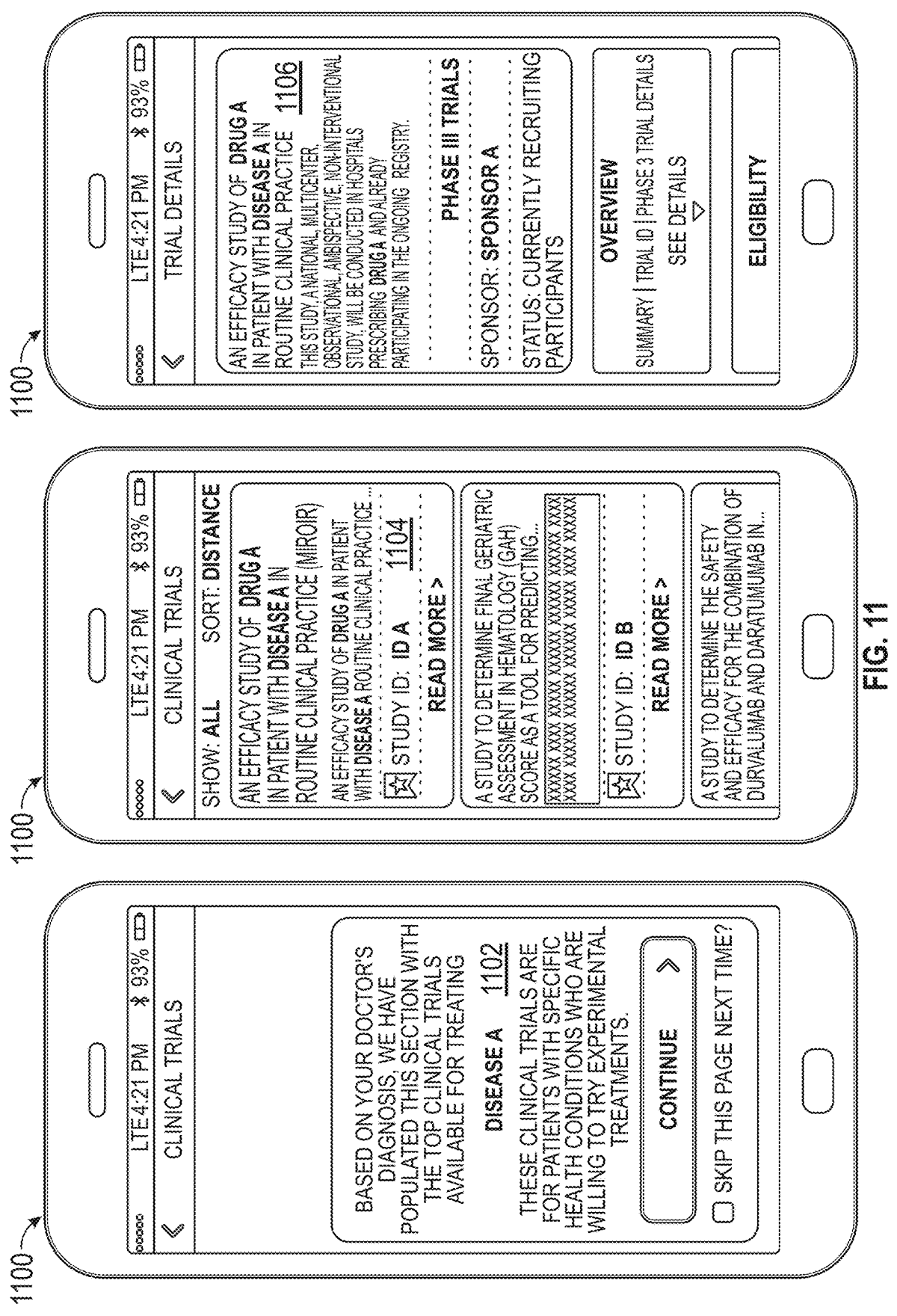

The user device can optionally allow patients to provide portions of their health records for use in clinical research. For example, the patients can indicate that clinical researchers are to be trusted with their health records such that clinical researchers can easily access medical information of patients. The health records can have personally identifiable information removed. The trust can be specified for a period of time, and upon completion of the clinical research, can automatically be revoked. In this way, clinical researchers can request particular types of patients they are interested in (for example, long-term smokers of a certain age), and corresponding patients can indicate trust via a simple usage of their user devices. Examples of clinical research available to a patient are illustrated in FIG. 11.

FIG. 1 illustrates systems involved in obtaining access to an example health record maintained by an example medical trust system 100. As described above, the medical trust system 100 can maintain health records of patients, and enable particular outside entities (for example, medical professional 154) to be trusted with access to portions of a health record. As illustrated, medical professional 154 is utilizing a user device 150 to access medical information of patient 'John Doe'. The user device 150 can include, at least, a mobile, device, a tablet, a wearable device, a laptop, a computer or any other electronic data exchange device. Optionally, the user device 150 may be a thin client, and the example medical information may be generated via a back-end web application. In this way, the user device 150 can access medical information utilizing only a web browser. Optionally, in this embodiment the medical trust system 100 may implement the web application and may route medical information from storage systems for presentation on the user device 150. The medical information is being presented in an application 160 and includes textual information 162 associated with a medical image 164. The application can include a web application associate with the medical trust system 100 running in a browser. The application can further include an application obtained from an electronic application store.

The application 160 may further be an example of an application configured to provide functionality to the medical professional 154. Differing applications may provide disparate functionality. For example, the application 160 may present medical images. A different application may be associated with prescribing medicine, viewing clinical research information aggregated from multitudes of medical records, billing information, and so on. Applications may further be automated, for example machine learning based applications may be utilized to request medical information and then analyze the medical information. Thus, the application may automatically request information from the system 100, for example access requests to information, via one or more Application Programming Interface (API) calls as described below. The application 160 may therefore be in an application layer. This application layer can represent applications configured to interact with the medical trust system 100 and provide front-end functionality to users. As described above, the user device 150 can execute a software agent 156 configured to directly communicate with the medical trust system 100. For example, the software agent 156 may communicate via a health communication protocol 120 as will be described in more detail below. The software agent 156 may provide information to the application 160, for example decrypted medical information, and receive information from the application 160.

As an example, the software agent 156 may respond to particular Application Programming Interface (API) calls received from the application 160. The software agent 156 may further respond to API calls from the health communication system 100. For example, the software agent 156 may receive a call from the system 100 indicating information (e.g., packets of information) are being routed to the application 160. The software agent 156 may respond to the system 100, for example optionally provide an acknowledgement, and may provide the received information to the application 160. As an example, the software agent 156 may provide the information via one or more API functions to the application 160. The application 160 may interact with the software agent 156 via defined API functions. Additionally, to provide information via the software agent 156 to the medical trust system 100, the application 160 may utilize particular API functions. As another example, the application 160 may provide an access request for information (e.g., medical information) to the medical trust system 100. For example, the application 160 may utilize particular API function calls which are provided to the system 100 via the software agent 156. The access request can indicate a request for authorization to access the requested information. The medical trust system 100 can then determine whether to authorize the request, for example based on trust information, and enable communication to one or systems storing, or responsible for access to, the requested information.

An example API function can include causing deletion of, or inaccessibility to, medical information presented on a user device via the application 160. For example, the medical information may be received via the software agent 156 over a health communication protocol 120 (described below). The medical information may be encrypted, and the software agent 156 may decrypt the information according to satisfaction of particular constraints. The software agent 156 may then provide access to the decrypted information to the application 160. The software agent 156 may then cause a loss of access to, or entire deletion of, the medical information. For example, the software agent 156 can cause the information to remain encrypted, and can constrain the application's 160 functionality. As an example, the software agent 156 can cause the application 160 to delete the decrypted medical information. Optionally, API function calls may be provided to the application 160 to enforce this deletion. An example of a loss of access to medical information, such as deletion, may include expiration of an authorization token associated with the user device 150. For example, access may be granted for a particular period of time, and the authorization token may be utilized to confirm identity of the medical professional 154. The software agent 156 may utilize the token to confirm identity, and then cause decryption of the medical information. Optionally, the authorization token may be utilized in the decryption process, such as via public key or private decryption. Optionally, the software agent 156 may utilize public key/private key decryption to decrypt medical information received from the system 100. Optionally, the software agent 156 may cause encryption of information received from the application 160, and may provide the encrypted information to the system 100.

To obtain the medical information, the user device 150 has provided a request 152 to the medical trust system 100 that indicates a request for the medical information. The request 152 can also indicate a request for particular types of medical information (for example, all x-ray images). As will be described in more detail below, with respect to FIG. 3, the medical professional 154 can have user account information associated with the medical trust system 100. For example, the medical professional can utilize his/her user device 150 to authenticate with the medical trust system 100 via associated user account information. User account information can include a user name and password. The medical trust system 100 can authenticate the medical professional 154, for example generate an encrypted access token to be provided to the user device 150. The encrypted access token can be included in subsequent request 152 from the user device 150 for access to medical information. In this way, the medical trust system 100 can determine that the medical professional 154 has already been authorized. Examples of encrypted access tokens include a JSON web token or an OAuth 2.0 token, and other encrypted access tokens can be utilized.

Upon receipt of the request 152, the medical trust system 100 can determine whether the medical professional 154 has been trusted to access medical information indicated in the request 152. As described above, a patient can authorize particular outside entities, such as medical professionals, to access portions of the patient's health record. The medical trust system 100 can store information describing trust, for example access control lists with respect to portions of a patient's health record, and can determine whether the medical professional 154 is authorized to access the medical information. Additionally, trust can be maintained by the medical trust system 100 according to role-based access controls. As an example, medical professionals of a same role, such as type of doctor, can be trusted with the same portions of a health record. Additional access controls can include discretionary access controls, and so on.

If the medical trust system 100 determines that the medical professional 154 is authorized to access the requested 152 medical information, the medical trust system 100 can access one or more databases or one or more storage subsystems (for example, record database 110), and obtain the medical information. The requested 152 medical information can then be provided to the user device 150 via a network and presented to the medical professional 154. The network can be, for example, the Internet.

Additionally, if the medical trust system 100 determines that the medical professional 154 is authorized to access the requested 152 medical information, the medical trust system 100 can establish a connection between the user device 150 and one or more outside systems that store the requested 152 medical information. For example, the medical trust system 100 can establish a connection between the user device 150 and the storage system. In this embodiment, the medical trust system 100 may not store medical information. For example, the medical trust system 100 may not store medical information in the record database 110. The medical trust system 100 may establish connections between systems, and route medical information over the connections. For example, medical information may be stored by one or more outside systems associated with a hospital. The medical trust system 100 may establish a connection between the outside systems and the user device 150. The medical trust system 100 can identify that the medical professional 154 is authorized to access the requested 152 medical information. As an example, the medical trust system 100 can determine that the medical professional 154 has been trusted with access to the requested 152 medical information. The request 152 can be provided to one or more outside systems storing the medical information, and the user device 150 can receive the medical information 102 via the established connection. For example, the medical information 102 can be received via the health communication protocol 120.

As illustrated, communications between the user device 150 and the medical trust system 100 are packaged according to a health communication protocol 120. The health communication protocol can be an application-layer protocol provided over a particular transport layer, such as User Datagram Protocol 'UDP' or Transmission Control Protocol 'TCP'. Optionally, the communications can be specific to a particular port, such as port 2047, 2041, or 1357, which is recognizable to the user device 150 and medical trust system 100 as being associated with the health communication protocol 120. Optionally, the communications can be over port 80, and medical information can be provided according to the hypertext transfer protocol (HTTP or HTTPS). For example, tunneling can be utilized such that the health communication protocol 120 is provided via data of the HTTP or HTTPS packets. In this way, if a firewall is utilized by an outside entity that blocks the particular port, medical information can be retrieved as HTTP network traffic via port 80.

The health communication protocol 120 can be utilized to easily identify that received information is related to medical information, and also to ensure that trust to the medical information is enforced. For example, upon confirmation that the requested 152 medical information can be provided to the medical professional 154, the medical trust system 100 can provide the medical information 102 back to the user device 150 in an encrypted form according to the health communication protocol 120. As will be described, the received medical information 102 can be inaccessible absent satisfaction of information (e.g., constraints) specified via the health communication protocol 120. For example, certain conditions or constraints must be recognized for access. The constraints may be specified by the medical trust system 100, for example based on a type of medical information being requested, based on a requesting application 160, an identity of a medical professional, a trust policy and so on. Optionally, the constraints may be specified by one or more storage systems that store requested medical information. For example, the when responding to an access request associated with a user device or application 160, a storage system may respond with requested medical information and can indicate constraints associated with usage of the requested medical information.

An example of the health communication protocol 120 is included in FIG. 1, and the example health communication protocol 120 includes portions 122-129. A portion can be associated with a header, such as identification information 122, and a message indicated by the header. The example portions 122-129 include identification information 122, authentication information 124, data 126, application data 128, and analytic information 129. Examples of each portion are included below; however, it should be understood that the features described for portions below can be combined into other portions, swapped with other portions, or not be included in the health communication protocol 120. Additionally, the health communication protocol may include additional portions not represented herein.

Each portion of the health communication protocol 120 may advantageously be generated by different systems within the medical trust system 100. That is, each portion may be generated and provided, for example via a virtual network channel, and combined prior to being provided as one or more packets to a user device. In this way, the portions of the protocol 120 may be kept separate, and interception of any one portion by an attacker of the system 100 is ineffective at accessing medical information being provided via the protocol 120. That is, the entirety of the portions can be required to access the medical information 120, for example as will be described.

Identification information 122 can include an identification of a medical professional authorized to access the medical information 102. Identification information 122 can include an identification of one or more user devices authorized to access the medical information 102. Identification information 122 can also include an identification of a valid time period in which the medical information 102 can be accessed. An example of the identification information 122 including an identification of the medical professional 154 is subsequently described. When requesting 152 medical information, the request 152 can include an encrypted access token associated with the medical professional 154. The medical trust system 100 can subsequently verify the access token, decrypt the access token, and verify a payload of the access token. The payload can identify the medical professional 154, and the medical trust system 100 can determine that the medical professional 154 is authorized to access the requested 152 medical information. The medical trust system 100 can provide encrypted medical information 102 to the user device 152 over the health communication protocol 120, with the health communication protocol 120 identifying the medical professional 154. In this way, the user device 150 can decrypt the medical information 102 upon verifying that an identity of the user of the user device 150 corresponds with the medical professional 154. As an example, the user device 150 can require that the medical professional 154 provide authentication information to the user device, such as account information, biometric information (for example, the medical professional 154 can be required to place his/her thumb on a thumbprint reader), and so on.

Additionally, the medical trust system 100 can maintain identifying information associated with user devices that the medical professional 154 utilizes, or that a location at which the medical professional 154 works utilizes. For example, the medical trust system 100 can obtain identifications of user devices that are authorized for the medical information 102 to be presented on. As an example, the identifications can include MAC addresses, globally unique identifiers 'GUID' s, CPU serial numbers, or identifiers associated with applications executing on the user devices. Optionally, the identification can be based on presence of an access token generated by the medical trust system 100. The applications can include applications utilized to provide requests 152 for medical information to the medical trust system 100. Upon receipt of the medical information 102 packaged via the health communication protocol 120, the user device 150 can obtain identifying information associated with the user device 150, and utilize the identifying information to decrypt the medical information 102. As described above, the software agent 156 may receive the medical information 102 and decrypt the medical information 102. Optionally, the health communication protocol 120 can further specify particular user identity, as described above.

The medical trust system 100 can also limit which types of user devices 150 are able to access particular types of medical information 102. For example, if the requested information 152 is a particular type of medical image the medical trust system 100 can indicate types of user devices which can present the particular type of medical image. An example type of medical image can be a single-photon emission computed tomography image, diffuse optical tomography, or any arbitrary complex imaging scheme. The medical trust system 100 can limit these types of medical images to being presented on computer systems that include software or hardware able to present the particular type of medical image. Therefore, the medical trust system 100 can cause mobile devices, laptops, or particular computer systems, to be unable to open these types of medical images. For example, the mobile devices, laptops, particular computer systems, can execute an application which can constrain access according to the protocol 120. The application may be the software agent 156.

In this way, the user device 150 can decrypt the medical information 102 upon determining that an identity associated with the user device 150 corresponds to the identification information 122. As an example, the user device 150 can include firmware (for example, encrypted firmware) associated with the medical trust system 100, and the user device 150 can obtain identifying information associated with the user device via the firmware.

Identification information 122 can further include information associated with a domain, such as a network domain, that is required to be utilized to access medical information 102. As an example, a domain may a network domain of a hospital, practice group, and so on, and accessing the medical information 102 can be predicated on the user device 150 being connected to the domain.

Authentication information 124 can include information associated with authenticating that the medical information 102 was received from the medical trust system 100. Authentication information 124 can include time information indicating a time period in which the medical information 102 can be decrypted. As an example of authenticating the medical trust system 100, when the user device 150 and medical trust system 100 begin communications, optionally one or more cryptographic protocols can be utilized to generate keys. For example, the cryptographic protocols can include Transport Layer Security or Secure Sockets Layer, and the generated keys can include encryption keys. The identity of the user device 150 and medical trust system 100 can optionally be encrypted, for example according to the encryption keys, and the identity of the medical trust system 100 can therefore be indicated in the authentication information 124. As an example, a message authentication code can be generated and included as the authentication information 124, with the message authentication code identifying the medical trust system 100. In this way, the authentication information 124 can be utilized by the user device 150 to ensure that the medical information 102 has arrived from a proper source or is related to the request 152 provided by the user device 150. Optionally, for any information provided via the protocol, each piece of information (for example, each packet provided via the protocol) can include different authentication information 124.

Additionally, the authentication information 124 can indicate a time period during which the medical information 102 can be accessed. For example, the medical trust system 100 can specify that the requested 152 medical information be accessible for a subsequent period of time. Example periods of time can include a same day, a subsequent week and so on. Optionally, time may be based on a uniform global time, such as provided by a governmental entity, a particular company, and so on. The medical trust system 100 can specify that the requested 152 medical information be accessible until a threshold number of accesses. For example, the medical information 102 can be limited to being accessed once, twice, or ten times before the medical information 102 will be inaccessible and need to be requested again.

The time period can be based on a type of medical information 102 being requested. For example, particular types of medical information may be larger (for example, larger in file size), and the time period can be increased with respect to other types of medical information. Therefore, a frequency with which the medical information is transmitted over a network can be reduced. Particular types of medical information may also be considered as being more sensitive such that a time period is reduced with respect to other types of medical information.

The time period can also be based on an identity associated with the medical professional 152 and/or user device 150. For example, particular medical professionals may be afforded lengthier time periods to access the medical information 152. An example medical professional commonly associated with a patient may be allowed to access medical information related to the patient for longer than a different medical professional. The medical trust system 100 can monitor occurrences of medical professionals with respect to accesses of medical information of patients, and can identify medical professionals that commonly access medical information of the patients. For example, a primary care doctor may commonly, for example greater than a threshold, more than an average, or greater than a threshold variance from an average, access medical information. Additionally, a patient can specify which medical professionals they more commonly see, or which medical professionals they prefer to allow longer access to his/her medical information. Optionally the time period can be a constant set by the medical trust system 100 such that all medical information is able to be accessed for a same amount of time. The time period can optionally be specified in a trust policy, which can be specified by a hospital, practice group, and indicate the time period.

Example use cases of a time period follow. An individual with a new diagnosis looking for novel trial enrollment. A machine learning application that can validate functionality historically, or with a larger data set. The application may be provided a onetime access for a single run, or until training is complete. This could be done on a third party server and could produce the output of an improved algorithm (e.g., a prediction application for readmission). For new insurance pricing, a user may ask for permission to look across a health record to drive more accurate actuarial underwriting (or possibly do this in real time changing how premiums are priced). This could be a onetime access. Another example relates to an individual patient who wants to inquire about a second opinion related to an image or set of labs. A medical professional could be allowed access for viewing specific medical information for a threshold number of times (e.g., 1, 2, 5) to allow for the second opinion to be rendered but the data to remain the property of others. Another example relates to patient transfer in an emergency situation. Another example relates to a prior CT scan that was done elsewhere recently as a baseline. Often currently medical professionals may not realize such CT scans exist. Thus, the medical professionals could be allowed access for comparison viewing, but CT scan wouldn't transfer systems.

Data 126 can include the medical information 102 to be accessed, for example as illustrated in FIG. 1, the data 126 can include the textual information 162, medical image 164, and so on. Additionally, the data 126 can be encrypted, and the user device 150 can decrypt the data 126. As described above in more detail, the decryption can be based on, for example, correct identification of the medical professional 154. Decryption can be based on correct identification of the user device 150. Additionally, decryption can be based on determining that a present time of access is within a particular time period, for example as described above. Thus, the health communication protocol 120 can safeguard against interception of network traffic received between a user device and the medical trust system 100.

Application data 128 can specify one or more applications that are able to present the medical information 102. As described above, the user device 150 can execute an application, and the application can present medical information 102, request 152 information from the medical trust system 100, and so on. Optionally, different applications can be utilized by different users, for example a patient may utilize a first application to access his/her medical information, while a medical professional can utilize a second application. Additionally, and as will be described, additional applications can be utilized by a billing department, scheduling department, insurance company, and so on. Optionally, the applications may be part of a same application, and can be modified according to a user operating the same application. That is, the user can provide authentication information, and the application can present a particular application (for example, a particular version) that corresponds with a user role of the user. Example user roles can include a patient, medical professional, billing department worker, insurance company worker, clinical researcher, and so on. The application data 128 can therefore require that a particular application be utilized to present the medical information 102.

Additionally, the application data 128 can specify particular applications necessary to present or access the medical information 102. For example, particular medical images, such as tomography images, may require particular software or hardware to be presented properly. The application data 128 can specify information indicating required software or hardware, such that the medical information 102 can be accessed. Examples of specified information can include identifiers associated with software or hardware.

Application data 128 can also specify applications able to provide requests for information to the medical trust system 100. As an example, and as will be described in more detail below with respect to FIG. 11, an application can be associated with presenting suggested clinical trials to patients. The application may provide requests to the medical trust system 100 indicating particular features or search queries. Example features can include smokers, patients greater than a threshold age, particular socioeconomic factors, and so on. The medical trust system 100 may parse the requests and analyze features of patients. The medical trust system 100 can then provide responses associated with the application, for example anonymized information. Therefore, the application data 128 can specify a particular application that is able to receive information being provided via the protocol.

The application data 128 can further be utilized by the medical trust system 100 to ensure that proper applications are receiving specific medical information. For example, the medical trust system 100 may receive an access request from a first application utilized to present particular types of medical images (e.g., three-dimensional images). The system 100 can obtain information from the access request indicating the request is for the particular type of medical image. The system 100 can then authorize the request, for example additionally based on trust information.

Analytic information 129 can indicate metadata associated with the medical information 102. Particular users, such as clinical researchers, can request analytics information related to health records maintained by the medical trust system. As an example, a user can specify particular filters identifying medical information, patients, or health records, for which the user is interested. The medical trust system 100 can then obtain information related to the filters. The filters can include, for example, a request for medical information associated with patients who are of a certain age or who meet certain criteria, and the medical trust system can obtain information to provide in response. Example criteria can include patients who are long-term smokers, overweight, from particular socio-economic backgrounds, or live in particular locations. As described above, this information can be anonymized by the medical trust system 100, with personally identifiable information removed, such that clinical researchers can gain the benefits of large quantities of data without patients exposing personally identifiable information. Additionally, the analytic information 129 can provide statistical information related to the data 126, such as information identifying recent accesses. The recent access information can describe accesses within a threshold amount of time, optionally identifying a medical professional that accessed the data. Statistical information can include features of the data 128, such as features of a patient, or a type of the medical information 102 (for example, DICOM images, and so on).

As described above, particular outside entities, such as hospitals or practice groups, can specify trust policies to be implemented when medical professionals associated with the outside entities access medical information. A trust policy can be maintained by the medical trust system 100, such that for any access to medical information, the medical trust system 100 can determine whether a trust policy is to be applied. Trust policies can also be specified by medical professionals or optionally by patients indicating access constraints to their health records. An example trust policy for the medical professional 154 can identify a particular user device 150 that is to be utilized to access the medical information 102, or a particular time period during which the medical information 102 can be accessed. A trust policy may specify that particular types of medical information, or all medical information, are not to be accessed on particular user devices (for example, a medical professional's personal computer, tablet, mobile device). Similarly, a trust policy can specify that medical information can only be accessed on user devices associated with an outside entity (for example, user devices located in a hospital). A trust policy can limit accesses to types of medical information to user devices that are associated with the same type of medical information. For example, x-rays may only be accessed on computer systems located in an area of a hospital in which x-rays are taken, or only accessed on computer systems which have been designated as being required for accessing x-ray images. A trust policy can also indicate a time period during which received medical information 102 can be accessible, and the trust policy may therefore require more frequent requests of information from the medical trust system 100. As an example, an outside entity may prefer knowing that all accesses to medical information of patients occurs closer in time to the actual time of request, thus safeguarding against improper access.

In this way, the medical professional 154 can access the received medical information 102 via the health communication protocol 120, and view the textual information 162 and medical image 164 identified in the medical information 102. For any updates that are made to the medical information 102, or additional notes generated by the medical professional 154, the medical trust system 100 can receive the updates and cause the updating of a corresponding health record. For example, the medical professional can utilize the application executing on the user device to update the medical information 102, generate and include additional information (for example, additional images, notes, and so on) via the application. The updated medical information 102 can be received by the medical trust system 100, and a patient's health record can be updated accordingly.

For updated, or additional, information received by the medical trust system 100, the medical trust system 100 can indicate that the information is to be trusted for future access by the medical professional 154. For example, the medical trust system 100 can cause updated, or additionally included, information to be automatically associated with the medical professional 154, such that no further trust action is required by the patient. Optionally, similar trust permissions can be updated for other medical professionals. For example, medical professionals part of a same outside entity, such as a hospital or practice group, as the medical professional 154, can be trusted with the updated information. As another example, medical professionals that have been trusted with a portion of a patient's health record that corresponds to the updated or additional, information can be similarly trusted with the updated or additional information. For example, a medical professional trusted by a patient to access general health information can update a portion of the general health information, and a different medical professional trusted by the patient to access the general health information can access the updates. Optionally, a trust policy can specify whether updates to medical information by a first medical professional are to be automatically trusted with other medical professionals. As an example, all medical professionals may be given access to updated drug allergy information.

As described above, the medical trust system 100 can enable connections between user devices and outside systems storing medical information. For example, the medical trust system 100 can generate a software-defined network. The software-defined network can enable connections via the health communication protocol 120. With respect to the updated medical information 102, the medical trust system 100 can receive the updates and provide them to one or more outside systems for storage. For example, the user device 150 of the medical professional 154 can receive updated information and route the updated information via the medical trust system 100.

Figure 2:
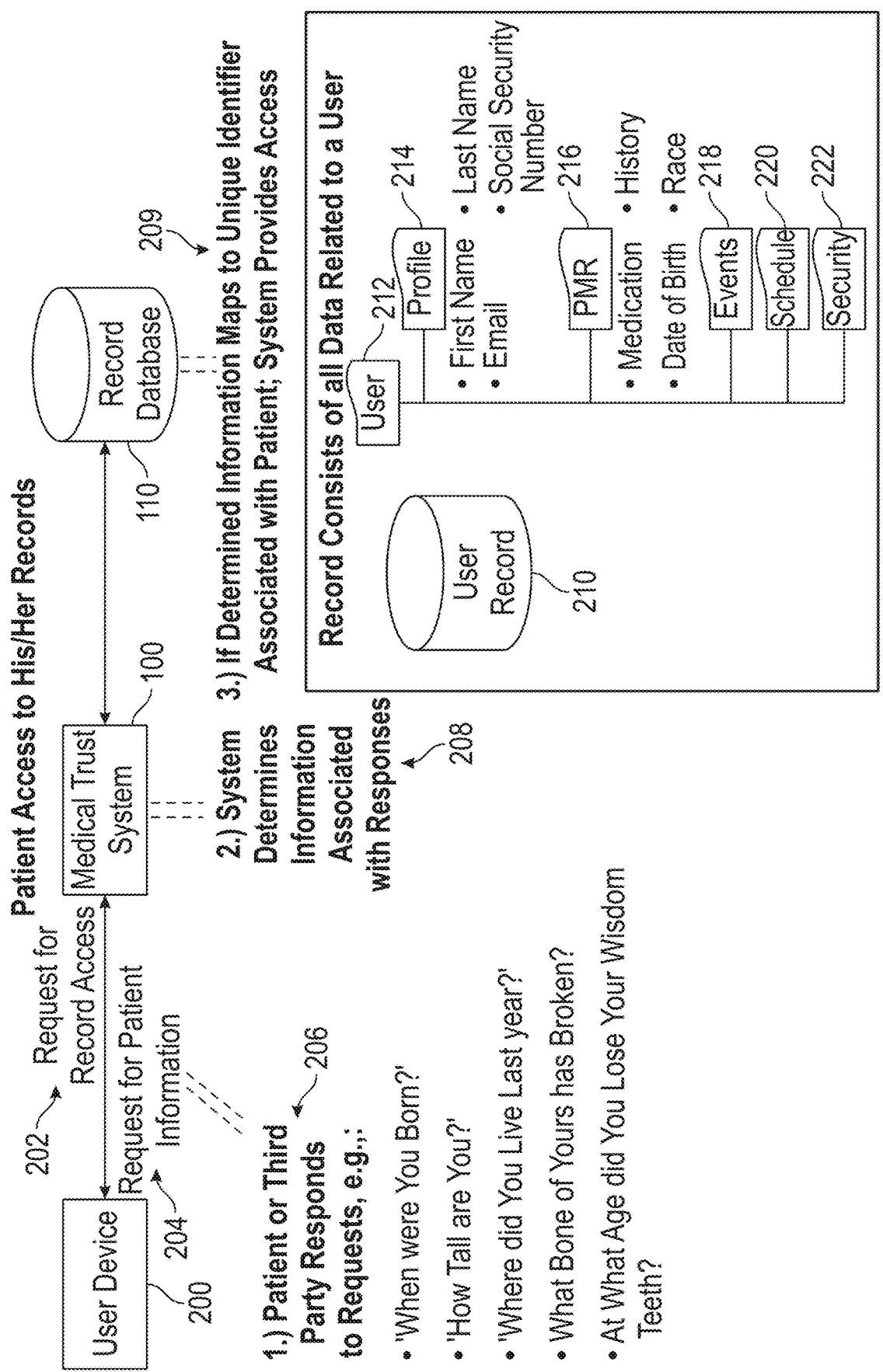
FIG. 2 illustrates a patient accessing a health record.

FIG. 2 illustrates a patient accessing a health record. As described above, a patient can access his/her health record, and enable outside entities, such as medical professionals, to access portions of the health record. The patient can utilize an application on a user device 200 to access the patient's health record, with the health record being maintained by the medical trust system 100. FIG. 2 illustrates a user device 200 being operated by a patient, and which is in communication with the medical trust system 100.

As described above, the medical trust system 100 may optionally maintain health records as being associated with a unique identifier (for example, an anonymized identifier). In this way, security related to the patient's health record can be increased, as medical information does not directly identify a patient's name. Optionally, the medical trust system 100 may store unique identifiers associated with patients but not store health records. In this embodiment, the medical trust system 100 can associate trust information with respective unique identifies. For example, the medical trust system 100 can store information identifying that particular medical professionals are trusted by a patient associated with a particular unique identifier. Additionally, the trust information can indicate particular portions of a patient's medical information that are trusted to particular medical professionals. Optionally, the trust information can indicate constraints associated with the trust. For example, a constraint can indicate that a first medical professional has read access but not write access. As another example, a constraint can indicate that a first medical professional can access a portion a threshold number of times. As another example, a constraint can indicate that a first medical professional can access a portion as long as the medical professional is employed by a same hospital, practice group, clinical research group, and so on.

As will be described, features which, in combination, uniquely (for example, within a threshold statistical percentage) describe a patient can be utilized by the medical trust system 100 to identify the patient. The medical trust system 100 can determine a unique identifier to assign the patient's health record based on the features uniquely describing the patient. When a patient first accesses his/her health record, the patient can be required to respond to requests for information. The requests for information can identify features of patients, and the medical trust system 100 can utilize the responses to uniquely identify the patient initially accessing his/her health record. Additionally, and as will be described, different requests for information can be utilized, with responses to the different features being mapped to different first identifiers, and all the first identifiers mapping to a second identifier uniquely associated with the patient. In this way, different features associated with the user can be utilized, and the same patient health record can be accessed.

Medical information for the patient can optionally be maintained without an express action by the patient to cause creation of the health record. For example, medical information associated with a patient may be maintained from a start of the patient's life, with additional information being included as the patient ages. The patient may assume control of the health record at any point, and until that point, the health record can be generated and maintained by the medical trust system 100. With respect to the example of a patient beginning life, features that uniquely describe the patient can include a time of birth, a location of birth, a hospital at which the patient was delivered, a doctor that delivered the patient, identification of the parents, and so on. A doctor that delivered the patient can utilize the medical trust system 100 to describe features of the patient, and the medical trust system 100 can create an associated health record for the patient. Optionally, the doctor may utilize a user device or system and describe features of the patient. The user device or system may cause generation of an associated health record, for example for storage by a hospital at which the doctor works. The medical trust system 100 may later establish connections between the user device or system for access to the associated health record. The created health record can be assigned a unique identifier based on features that uniquely describe the patient. As the patient ages, additional features can be utilized to uniquely describe the patient, and additional information can be included in the same record. For example, a subsequent doctor can access the patient's health record via indicating features of the patient, and the subsequent doctor can include information in the patient's health record. The subsequent doctor may be required to respond to request for information from the medical trust system 100 to identify the patient. Optionally, the subsequent doctor can provide features of the patient, and the medical trust system 100 can determine whether a health record in conformance with the features is being maintained.

The patient may, as will be described, access his/her health record, or optionally cause generation of a new health record, and the medical trust system 100 can provide access to the patient's health record. Optionally, additional proof may be required for the patient to access his/her health record, and upon satisfaction of the additional proof the patient may assume control of the health record. Additional proof can include a driver's license, passport, address, social security number, and so on.

A health record of a patient can be separated into chunks of information, which may optionally be separately maintained by the medical trust system 100 (for example, stored on different systems, storage devices, and so on). Each chunk of information can reference a unique identifier assigned to the patient's health record. The patient's personally identifiable information 214, for example with respect to the patient's health record 210, can similarly be separated as one or more chunks of information that reference the same unique identifier.

Medical information of a patient may be separated into chunks of information, with the chunks spread across disparate outside systems or user devices. The medical trust system 100 may provide access to medical information via establishing connections between the user device 200 and the outside systems or user devices. For example, the user device 200 may execute an application, such as a front-end application associated with healthcare. The front-end application may communicate with an application associated with the medical trust system 100, for example a software agent, and the application may provide requests to the medical trust system 100 for access to one or more of the chunks of information. Based on determining that the patient 200 is authorized to access the chunks, the medical trust system 100 can authorize the front-end application's request for medical information, and provide the request to outside systems or user devices which can respond to the request. For example, the request can be provided via the health communication protocol. Optionally, the front-end application's request may specify locations at which the requested medical information is stored. As an example, a specified location may comprise a particular outside system or user device. Thus, the medical trust system 100 can provide the request to the specified outside systems or user devices.

FIG. 2 illustrates a user device 200 of a patient requesting access 202 to the patient's health record. Upon receipt of the request 202, the medical trust system 100 can determine whether the patient is authorized to access the health record. For example, patients can create user account information with the medical trust system 100, and the medical trust system 100 can utilize the user account information to determine whether the patient can access the health record. As an example, the medical trust system 100 can store information identifying that the patient's user account information is associated with his/her health record. The request 202, for example, may also indicate that the patient does not have user account information with the medical trust system 100, and the medical trust system 100 may therefore cause the patient to indicate his/her identity. For example, a first time that the patient utilizes an application associated with the medical trust system 100, the request 202 can indicate that the patient does not have user account information.

If the patient does not have user account information, the user device 200 can provide (for example, present via a display, output via speakers, and so on) requests for information 204 that describe an identity of the patient. The requests for information can include features of the patient that, in combination, uniquely describe the patient. The medical trust system 100 may select from a multitude of features, and provide information identifying each feature to the user device. The user device can then present the received features as requests for information. For example, the patient can respond to example requests for information 206 such as, 'when were you born?', 'how tall are you?', 'where did you live last year?', 'what bone of yours has broken?', 'at what age did you lose your wisdom teeth?' and so on. Biometric information can also be used to identify the user including, for example, fingerprint data obtained from the user device, voice recognition data, facial recognition or other biometric information. The features selected by the medical trust system 100 may be selected absent any knowledge of the patient, and may be selected to, in combination, uniquely identify an identity of the patient. That is, with a sufficient number of features of a person, the person can be uniquely identified with respect to all other persons. The medical trust system 100 can utilize the responses 206 to identify a patient that corresponds to the responses. For example, even if a patient had not created user account information with the medical trust system 100, the medical trust system 100 may have a health record of the patient via his/her prior visits to medical professionals.

Upon receipt of the responses 206, the medical trust system 100 can determine information 208 associated with the responses. For example, the medical trust system 100 can compute a particular hash based on the responses, or otherwise combine the responses, to generate a value (for example, a number). Example hashes can include cryptographic hashes, such as SHA-256, MD5, SHA-3, and so on. The medical trust system 100 can then determine whether the determined information 208 maps to an identifier of a patient (for example, indexes a health record, such as a top node of a health record 212). Optionally, the medical trust system 100 can examine metadata associated with health records, and compare the responses to the metadata. Metadata can include features identified in health records.

As illustrated in FIG. 2, if the determined information 208 maps to a unique identifier associated with a patient's health record, the medical trust system 100 can provide access to the health record 209. That is, the medical trust system 100 can determine whether a health record was indexed by the unique identifier, and if so, can provide access to the health record. Optionally, the medical trust system 100 can allow the patient to create user account information, such that in future requests for access to the patient's health record, the patient can supply the user account information.

An example of a health record 210 is illustrated, with the health record 210 being indexed by a unique identifier 212. For example, the health record 210 may be stored by an outside storage system, or may be stored in a database accessible by the medical trust system (e.g., record database 110). As described above, the health record 210 can include chunks or portions of data referencing the unique identifier 212, and as illustrated, the health record is separated into chunks 214-222. Each of the chunks 214-222 can be further separated into smaller chunks, and the smaller chunks can reference a parent chunk and the unique identifier 212. The chunks 214-222 can, optionally, be utilized to describe a basic separation of a patient's health records. For example, personally identifiable information 214, such as name or social security number, can be separated from the patient's medical history (PMR) 216. Additionally, chunks can include events 218—identifying particular medical occurrences, a schedule 220—identifying a schedule of the patient, for example separated according to outside entity, security 222—user account information, authentication information, and so on. Breaking up the information can increase security of the information by making it more difficult to easily link one accessed date chunk with another. As described above, the health record 210 may be stored by one or more outside systems. In this embodiment, the medical trust system 100 may establish a connection to the outside systems, and route requested patient information 204 to user device 200. For example, the medical trust system 100 can route the information 204 over the health communication protocol.

Prior to access of his/her health record 210, a medical professional or other third party may be required to confirm an identity of the patient. For example, the patient can respond to the questions, but only upon confirmation by a medical professional will the patient be allowed access. Optionally, the medical professional can be authorized with respect to the system (for example, an identity of the medical professional can be previously determined). The medical professional can specify trust is to be provided to the patient, and the patient can then be afforded access to the health record 210. Optionally, the medical professional may be required to provide answers to requests for information related to the patient. For example, the medical professional can answer the same questions, and based on the answers, the patient can be authorized. In this way, an identity of the patient can be ensured to be accurate.

After accessing his/her health record 210, the patient can indicate trust of each chunk 214-222 to particular outside entities, such that the outside entities can access the chunks, update the chunks, include new information associated with trusted chunks, and so on. Trust can be further indicated via application of a trust policy. For example, the patient can indicate trust to an outside entity, such as a hospital or practice group, and medical professionals within the outside entity can receive trust. Trust to particular portions of the health record 210 can be assigned based on the patient's initial indication of trust to a medical professional. For example, the patient can indicate trust to a podiatrist, and the podiatrist can automatically be trusted with particular portions of the health record 210.

Particular portions of the health record 210 may be edited by the patient, while other portions may not be edited by the patient. As an example, findings or notes specified by medical professionals may be maintained in the health record 210, and the system 100 may not allow edits of the information by the patient. Similarly, when a patient indicates trust to a medical professional, the trust may automatically specify portions of the health record 210 that are to be trusted with the medical professional. In this way, the system 100 can limit a patient's ability to hide or otherwise edit information, ensuring that information is accurate within the health record 210.

The patient may indicate trust to third parties not in the context of medicine, and can effectively assume a unique persona outside of the medical professional context. In this context, the patient may wish to hide certain information included in his/her health record 210. This unique persona can be referred to as a personal persona, and the patient can have greater autonomy with respect to modifying or hiding portions of a health record 210. However, the patient's medical persona may be more constrained. For example, and as described above, in the context of medicine the patient may be disallowed from hiding certain information included in the health record 210 or editing the information.

As described above, the patient's health record can be maintained as chunks of data. The medical trust system 100 can, in response to requests, generate combinations of information from the chunks and provide information on the fly in response. The response can include particular chunks of information and/or versions of information, and can be separated into packets to be provided via the health communication protocol. Only upon receipt of the packets by a device or system can the information can be generated from the packets on the fly, and access to the requested medical information be provided. In this way, the system can limit an attacker from snooping or otherwise obtaining medical information.

Optionally, the health record 210 can be stored in different systems in differing locations. For example, hospitals and/or medical groups may store portions of the health record 210 that are updated by respective medical professionals. As an example, a first portion of the health record 210 related to feet may be stored by systems related to a podiatry medical practice group. In this way, the hospitals and/or medical groups can utilize their own local storage to store medical information. The medical trust system 100 can store information, such as references, indicating locations at which portions of the health record are stored. Additionally, the medical trust system 100 can cache the portions such that access times can be reduced. The systems that store portions of the health record 210 may be required to execute software associated with the medical trust system 100. For example, the systems may be required to authenticate with the system 100, utilize the health communication protocol in responding to requests for access to medical information, and so on.

Figure 3:
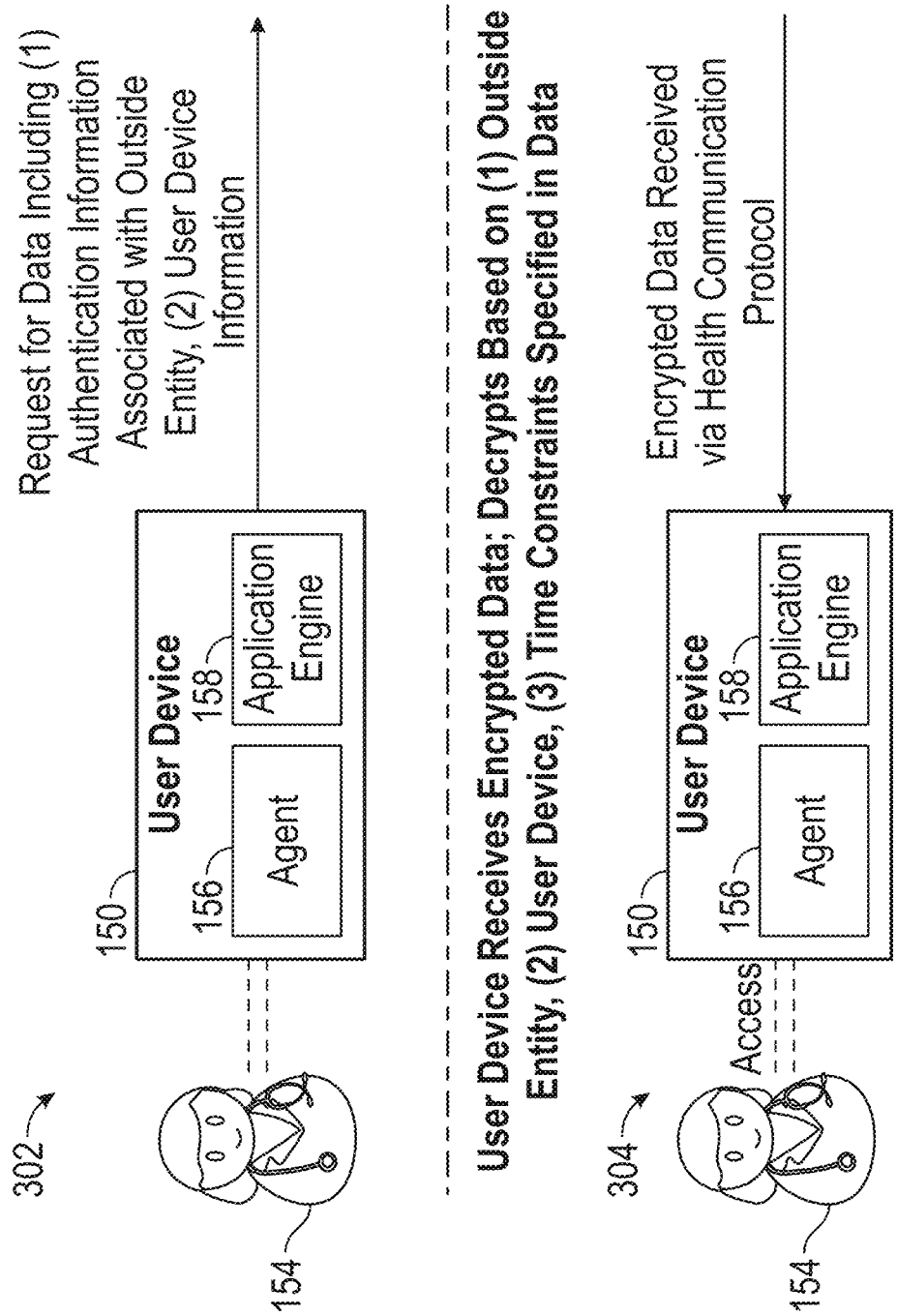
FIG. 3 illustrates a medical professional accessing a health record.

FIG. 3 illustrates a medical professional 154 accessing a health record. As illustrated in FIG. 2, a patient can access his/her health record, and indicate trust to portions of the health record to outside entities, such as medical professionals. An outside entity, such as medical professional 154, can then utilize an application executing on a user device (for example, application engine 158), and access trusted portions of the patient's health record.

As illustrated in portion 302 of FIG. 3, a medical professional 154 is utilizing a user device 150 to request data regarding a patient's health record. For example, the user device 150 can present a user interface of an application, and the medical professional 154 can provide authentication information via the application for receipt by the medical trust system 100. The application may be an example of an application obtained via an application store. The application may further be a locally installed application or a web-application. The medical professional 154 can utilize a particular application according to desired functionality. For example, different applications may be associated with disparate functionality. The medical trust system 100 can respond to access requests from the different applications, and as will be describe service the requests. Optionally, a software agent associated with the medical trust system 100 may route information between the application and the medical trust system 100 over the health communication protocol. Authentication information can include user account information, such as a user name and password with the medical trust system 100, biometric information, and so on. As an example, the medical professional 154 can provide his/her user name, password, and interact with a user interface of the application to cause the user device 150 to provide a request to the medical trust system. The request can include the user name and password, optionally along with user device information (for example, an identifier associated with the user device).

As described above, with respect to FIG. 1, the medical trust system 100 can determine whether the received authentication information is valid, and upon authentication, can generate an encrypted token to be provided to the user device 150. The encrypted token can thereafter identify the validity of the medical professional 154 to the medical trust system 100.

As illustrated in portion 304 of FIG. 3, the medical professional 154 has requested a portion of a patient's health record, and received encrypted data over the health communication protocol. The medical professional 154 can utilize the application to identify a particular portion for which the medical professional 154 is interested. As an example, the application can present information identifying patients that the medical professional 154 can access, or optionally the application can allow the medical professional 154 to enter a name of the patient. The medical trust system 100 can receive an identification of a patient, and determine whether the medical professional 154 has been trusted with access to at least a portion of the identified patient's health record. Upon a positive determination, the medical trust system 100 can optionally provide information identifying portions of the health record that the medical professional has been trusted to access, and the medical professional can select from the portions 154. Optionally, the medical trust system 100 can provide information identifying all patients that the medical professional is able to access, along with information identifying trusted portions of each associated health record. In this way, the medical professional can easily identify a particular patient, along with one or more portions of information, and the medical trust system 100 can obtain the portions.

Subsequent to selection of a patient, and portions of the patient's health record, the user device 150 can receive encrypted data (for example, requested portions of the patient's health record) over the health communication protocol. As described above, with respect to FIG. 1, the health communication protocol can indicate constraints on access to the requested data. The constraints can include constraints with respect to a user device 150 used to present the data, a constraint with respect to an identity of the medical professional 154, time constraints, and so on.

In addition to the medical professional 154 identifying a particular patient and one or more portions of the patient's health record to access, the medical professional 154 can request all trusted portions. The medical professional 154 can further provide a query indicating information the medical professional 154 is interested in, and the medical trust system 100 can obtain matching information from the particular patient's health record. For example, the medical trust system 100 can provide the query to one or more storage systems storing medical information. The storage systems can process the query and provide matching medical information. As an example, the medical professional 154 can request allergy information (for example, drug allergies), and the medical trust system 100 can identify any previously identified allergies. The medical trust system 100 can optionally parse any received medical information, and include the parsed medical information into particular chunks, such that allergies can be maintained in a same chunk. The medical trust system 100 can further run a keyword search of all received medical information to identify drug allergies. In this way, the medical trust system 100 can respond to complex requests for information. An example request can include 'provide me [medical professional] with all x-rays taken in the past month'. An additional example request can include 'provide me with all x-rays taken since the patient broke her arm'. In this additional example, the medical trust system 100 can identify that 'since the patient broke her arm' indicates a request for a date. The system 100 can then determine a date associated with the broken arm, and can obtain all x-rays taken since the date.

While the system can allow a medical professional to utilize an application to select a particular patient, the medical trust system 100 can be limited such that the medical trust system 100 alone can utilize unique identifiers associated with health records. When the medical trust system 100 authenticates a medical professional, the medical trust system 100 can access information identifying unique identifiers associated with health records that the medical professional can access. The medical trust system 100 can then access a particular chunk of data indexed by the unique identifiers that specifies respective names of associated patients. The names can then be provided to the medical professional, who can select from among the names, and upon selection, the medical trust system 100 can provide trusted portions of a corresponding health record. In this way, personally identifiable information of patients are treated merely as data, and references to health records are via unique identifiers.

Figure 4:
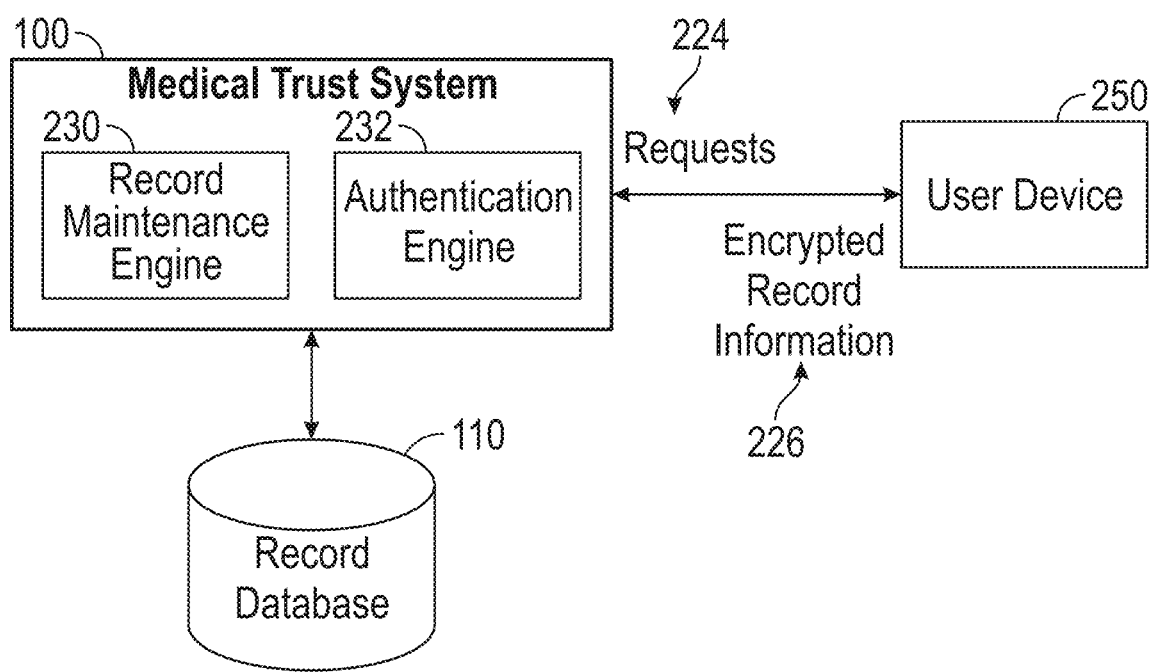
FIG. 4 illustrates a block diagram of a medical trust system in communication with a user device.

FIG. 4 illustrates a block diagram of a medical trust system 100 in communication with a user device 250. The medical trust system 100 can be a system of one or more computers (for example, computer systems implementing a cloud-based system), and/or one or more virtual machines executing on a system of one or more computers. The medical trust system 100 can respond to requests 224 for access to health records of patients, and can provide encrypted information 226 in response to the requests 224.

The medical trust system 100 includes an authentication engine 232 that can maintain authentication information associated with outside entities, such as medical professionals. That is, medical professionals can utilize the medical trust system 100 to create a user name and/or password such that the medical professionals can send requests 224 for information from the medical trust system 100. Additional authentication information can include biometric logins, use of two-factor logins, and so on. The authentication engine 232 can additionally generate access tokens. For example, access tokens can be generated in response to a medical professional utilizing the user device 250 providing authentication information, such that medical professionals can utilize the access tokens to request 224 information.

The medical trust system further may optionally include a record maintenance engine 230 that can maintain health records of patients (for example, in record database 110), and can enable medical professionals to access health records. As an example, and with respect to the health record 210 illustrated in FIG. 2, the record maintenance engine 230 can store patient's health records as chunks of data, with each chunk including a reference to a same identifier. The record maintenance engine 230 can optionally store medical information in particular chunks according to included information. For example, when medical professionals are generating information to be included in a patient's health record, the medical professionals can utilize an application executing on their respective user devices. The application can optionally provide standard templates for medical professionals to utilize for inputting of information. For example, the application can enable 'Meaningful Use', such as Meaningful Use Stages 1, 2, 3. The record maintenance engine 230 can receive information according to the formats, and include information in corresponding chunks of the health record. As an example, the record maintenance engine 230 can indicate a chunk as being associated with drug allergies, or can indicate a chunk as being associated with medical images or types of medical images, and so on. In this way, portions of a health record can be trusted to medical professionals, with the portions being specific to particular information.

Additionally, and as described above with respect to FIG. 2, the record database 110 can store information indicating locations at which portions of a health record are stored. For example, the record database 110 can indicate that x-rays of a particular patient are stored on server systems associated with a particular hospital. In this way, the medical trust system 100 can avoid storing medical information. Instead the medical trust system 100 can obtain medical information from appropriate storage systems. Optionally, locations at which portions of a health record are stored can be provided in access requests received from user devices. For example, an application may execute on a user device that is associated with presenting and updating medical records. The application may be associated with one or more storage systems. Upon receipt of a request for medical information, the request can indicate locations of the storage systems. The medical trust system 100 can provide the request to the storage systems, for example via the health communication protocol. Optionally, the medical trust system 100 may maintain locations (e.g., network locations) of portions of each patient's medical information. For example, the medical trust system 100 may store a unique identified associated with each patient, and additionally locations of portions of the patient's medical information. Optionally, each portion may be referenceable according to a unique identifier, feature keywords (e.g., describing a type of information stored therein), and so on. In this way, the medical trust system 100 may provide received requests to a proper storage system.

As described above, the medical trust system 100 can maintain versions of health records, such that changes to a patient's health record can be monitored. As will be described below with respect to FIG. 8, the medical trust system 100 can generate snapshots of a patient's health record for arbitrary dates. The record maintenance engine 230 can therefore monitor changes to a patient's health record, and indicate timestamps associated with changes along with information identifying the change. In this way, if the patient indicates that a particular outside entity is no longer to be trusted, the medical trust system 100 can sever the trust, and the particular outside entity can be limited to accessing a snapshot of the patient's health record as it existed when the trust was severed. Severing trust can include, for example, de-authorizing the outside entity. The patient can then establish trust with a different outside entity (for example, the patient can switch doctors), and the different outside entity can be trusted with an up-to date version of the patient's health record.

Figure 5:
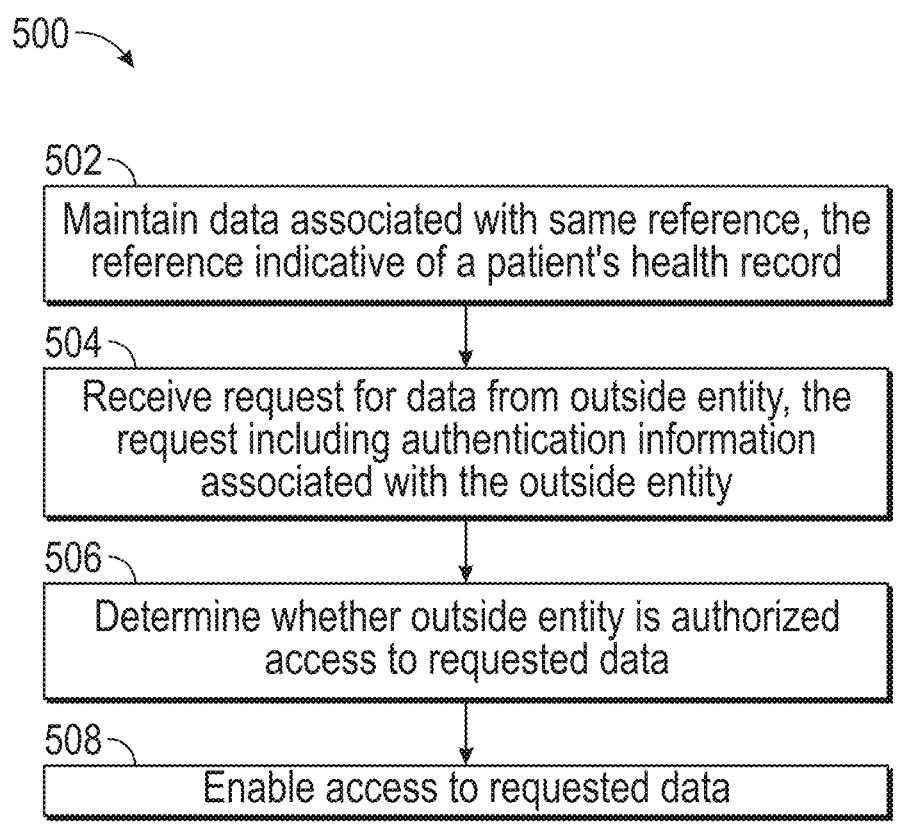
FIG. 5 is a flowchart of an example process for enabling access to a health record.

FIG. 5 is a flowchart of an example process 500 for enabling access to a health record. For convenience, the process 500 will be described as being performed by a system of one or more computers and/or servers, including for example, the medical trust system 100.

The system maintains data associated with a patient's health record (block 502). As described above, with respect to FIG. 2, the system can maintain health records, with each health record associated with a particular unique identifier. Each health record can be indexed by the particular unique identifier. Personally identifiable information associated with each health record can be similarly indexed by a unique identifier, such that the personally identifiable information is treated as arbitrary stored data, and not utilized as an index to the health record. Personally identifiable information can include a patient's name, address, social security number, and so on.

As also described above, with respect to FIG. 2, the system can determine the particular unique identifiers for the health records based on features of associated patients. For example, the system can utilize a patient's address at a particular time in his/her life, a name of a prior doctor, a medical accident that occurred to him/her, and so on, such that the patient can be uniquely identified without providing a name, social security number, and so on. From these features, the system can determine a unique identifier, and all information associated with a person that corresponds to those features can be maintained in the same health record. The system can determine a multitude of mappings, for each patient, from the determined unique identifier to identifiers computed based on different features associated with the patient. For example, the system can determine a first identifier according to first features (for example, name of prior doctor on particular date, particular address, and so on), and can determine a second identifier according to second features (for example, name of prior doctor on particular date, an identification of a particular medical accident). Since both the first features and the second features uniquely describe a same person, the system can determine a same health record that matches the first features and second features. The system can therefore maintain mappings of all sets of features (for example, the first features and second features) to the determined unique identifier associated with the patient.

The system receives a request for data from an outside entity (block 504). As described above, the outside entities can interact with user devices to provide requests for trusted portions of data. For example, the outside entity can execute an application, and interact with the application to provide authentication information for verification by the system. The request can further indicate portions of a health record for which the outside entity is trusted to access, or optionally other information including an identification of all portions the outside entity is trusted with, an identification of all patients the outside entity can access, and so on.

The system determines whether the outside entity is authorized access to requested data (block 506). Upon receipt of the authentication information, the system can access maintained user account (for example, user profile) information, and can authenticate the outside entity. Additionally, the system can authenticate the user device, for example determine that the user device is associated with the outside entity. A user device associated with the outside entity can include a user device known to be utilized by the outside entity. If the user device is not known to be utilized, the system can require the outside entity to confirm the user device utilizing a different user device known to the system, or register the user device for use with the system. Optionally, the system can utilize location information associated with the requesting user device (for example, an IP address), and can compare the location information to known locations from which the outside entity accesses the system. If the system determines that the user device is being used at a known location, it can optionally authenticate use of the user device by the outside entity.

After authenticating the outside entity, the system can optionally determine health records for which the outside entity has access. As described above, the system can maintain identifications of health records for which each outside entity has been trusted. These identifications can reference (for example, the identifications can be pointers) unique identifiers associated with patient health records, and for example, not reference personally identifiable information associated with the patients. Example identifications can be pointers. In this way, the system can utilize each reference to access corresponding health records. For example, the references can be utilized to index health records, such as via a database key-pair lookup. In this way, each outside entity's user account information can limit an extent to which the information directly references patients' personally identifiable information.

The system can therefore determine whether the outside entity is authorized to access the requested data. As described above, portions of the patient's health record can individually indicate access rights to the portions. This can occur, for example, through use of access control lists. The system can determine whether the outside entity is indicated as being trusted with respect to the requested data. Optionally, the system can utilize role based access controls and determine whether a role associated with the outside entity has been assigned access rights to the requested data. As an example, a podiatrist may be given access to a first portion(s), while a radiologist may be given access to a second portion(s). In this way, a patient can indicate trust to an outside entity, and the system can determine portions of the patient's health record to be trusted with the outside entity according to the outside entity's role. Additional methods of constraining, controlling, access to data can also be utilized.

The system enables access to the requested data (block 508). The system, upon determining that the outside entity has been trusted with the requested data, provides access to the requested data. Access can include providing the requested data to the user device of the outside entity via the health communication protocol. The health communication protocol is described in more detail above, with respect to FIG. 1.

Optionally, access can include providing a modified version of the requested data. For example, the system can determine that the user device being utilized to access the requested data is a mobile device and/or is communicating over a network with limited bandwidth. The system can then modify a quality aspect of the requested data. As an example, a quality aspect can include adjusting a resolution of medical images, such as reducing resolution, compressing the medical images, and so on. The system can optionally obtain information identifying a size of a display of the user device, and reduce the resolution based on the size. The outside entity can optionally request an unmodified version of the requested data.

The system can provide the requested data via the health communication protocol. For example, the system can indicate that only the outside entity, and optionally the requesting user device, can access the requested data. Optionally, the system can further indicate that other user devices can access the requested data, such that the requested data can be securely shared. For example, the received data can be shared, and only presented on authorized user devices.

Upon receipt of the requested data, the user device of the outside entity can present the requested data via an application executing on the user device. As described above, the user device of the outside entity can further verify that the user device can present the received data. For example, the user device can decrypt the requested data according to constraints indicated in the health communication protocol.

Figure 6:
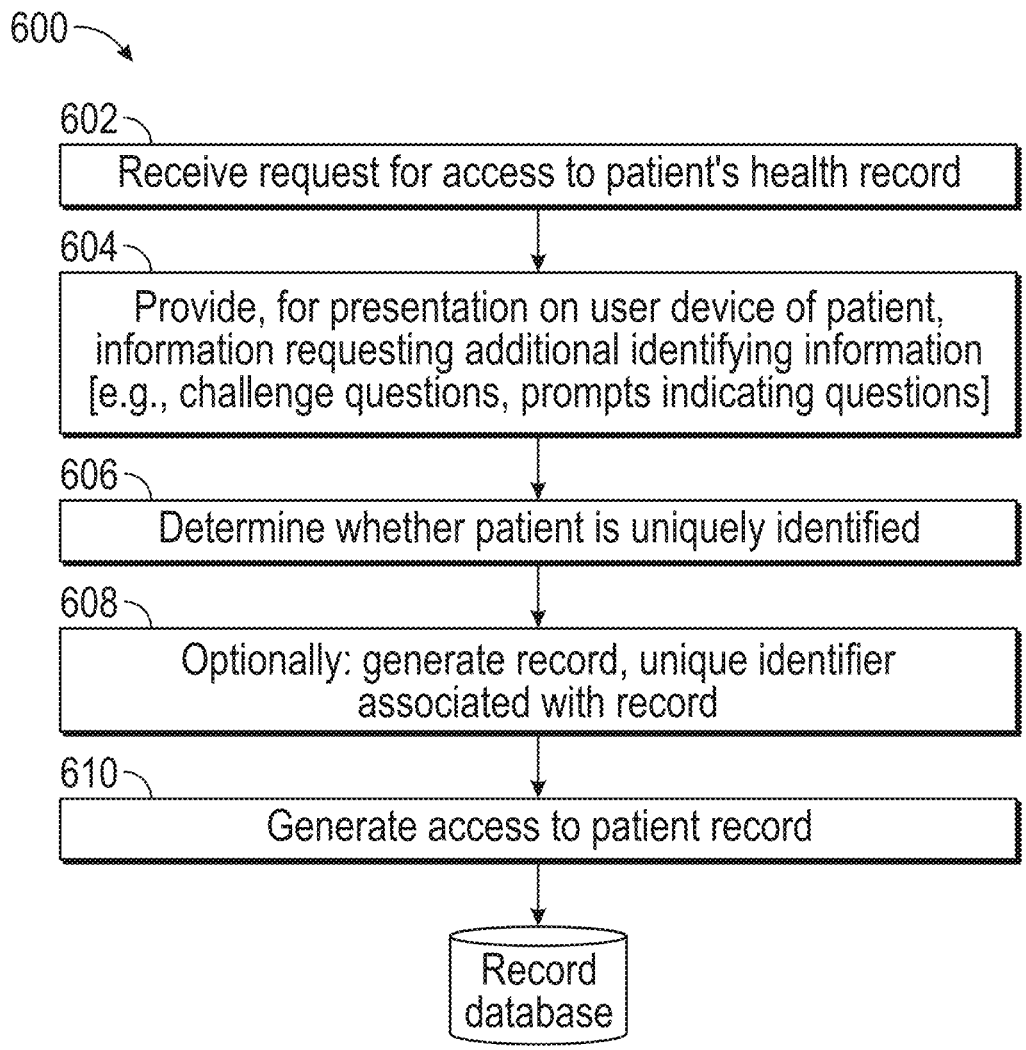
FIG. 6 is a flowchart of an example process for patient access to his/her health record.

FIG. 6 is a flowchart of an example process 600 for patient access to his/her health record. For convenience, the process 600 will be described as being performed by a system of one or more computers and/or servers, including, for example, the medical trust system 100.

The system receives request for access to a patient's health record (block 602). As described above, with respect to FIG. 2, a patient can utilize an application associated with the system, and can request access to his/her health record. For example, during an initial use of the application, the patient may be trying to create user account information with the system. The system can determine whether the patient corresponds to a health record being maintained by the system.

The system provides, for presentation on a user device of the patient, questions describing features of patients (block 604). As described above, with respect to FIG. 2, the system can present questions to patients identifying features of patients that are sufficient to uniquely identify a patient. For example, the system can compare responses to the questions to information indicated in maintained health records. Biometric information can also be used to identify the patient as described above. The system can determine whether a particular patient corresponds to the responses. Optionally the system can utilize other information, for example location information associated with the patient, to determine a corresponding medical record. As an example, if the system identifies more than one patient based on the responses, the system can utilize the location information to determine a more likely candidate. The system can then present one or more additional requests for information from the patient to verify that the patient is the more likely candidate. The patient can also be required to present themselves to a trusted administrator to further verify the user.

The system can maintain questions to provide to patients, and the system can select a threshold number from the maintained questions to be provided to the user. For example, the system can obtain indications of sets of questions that are sufficient to identify patients, and can utilize a set of questions selected from among the sets to provide to the patient. The chosen set of questions can be random or selected based on information in the request. Optionally, the system can request basic information from the patient prior to selecting the questions. For example, the basic information can include an age of the patient, such that the system can select age-appropriate questions.

The system determines whether the patient is uniquely identified (block 606). The system obtains the responses to the requests, and compares the responses to information associated with health records. For example, the patient can enter responses on his/her user device, and the user device can provide the responses to the system. The communications can be made via an encrypted session to maintain security. Optionally the system can maintain metadata associated with each health record. For example, particular features from the health record. The metadata can be used to rapidly compare the metadata to the responses. If the system finds a matching health record, the system can indicate that the patient corresponds with the health record. In contrast, if the system does not find a matching health record, the system can request additional information from the patient (for example, the patient may have entered a response incorrectly), and can attempt to find a matching record again. However, if a health record does not exist for the patient, the system can generate a health record for the patient. In this way, if the patient sees outside entities, such as doctors, the outside entities can provide medical information to the generated health record. For example, the patient can indicate trust to a doctor and the system can update user account information associated with the doctor to indicate the trust to the health record. The doctor can then update the health record.

The system can enable the patient to create user account information with the system, for example a user name and password. The created user account information can reference the health record. For example, the account information can reference a unique identifier associated with the health record. When the patient subsequently accesses the system, the system can determine a corresponding health record based on the unique identifier.

The system optionally generates a record and unique identifier associated with record (block 608). As described above, if the system does not maintain a record associated with the patient, the system can generate a new record and/or determine a unique identifier to associate with the record. Optionally, the unique identifier can be generated from the features which unique describe the patient (for example, a hash can be computed from the features), or the unique identifier can be an arbitrary value (for example, a random number). As described above, the system can maintain multiple mappings from responses to requests for features of a patient to a same health record associated with the patient. For example, and as will be described below with respect to FIG. 7B, a patient can indicate trust to an outside entity, such as a medical professional. However, optionally the medical professional can identify a patient (for example, prior to seeing the patient) and request trust from the patient. The system can notify the patient, for example via an application executing on patient's user device, and the patient can confirm trust to the medical professional. In this scenario, the medical professional can provide features of the patient to the system to uniquely identify the patient, and the system can determine a corresponding health record of the uniquely identified patient. The system can then notify the patient of the medical professional's request.

The system generates access to the patient record (block 610). As described above, the system can indicate in user account information of the patient that the patient is associated with the patient record. For example, the system can indicate that the user account associated with the patient has full access rights to the medical record, including rights to trust portions of the medical record with outside entities. The system can then update one or more databases or one or more storage subsystems.

Figure 7A:
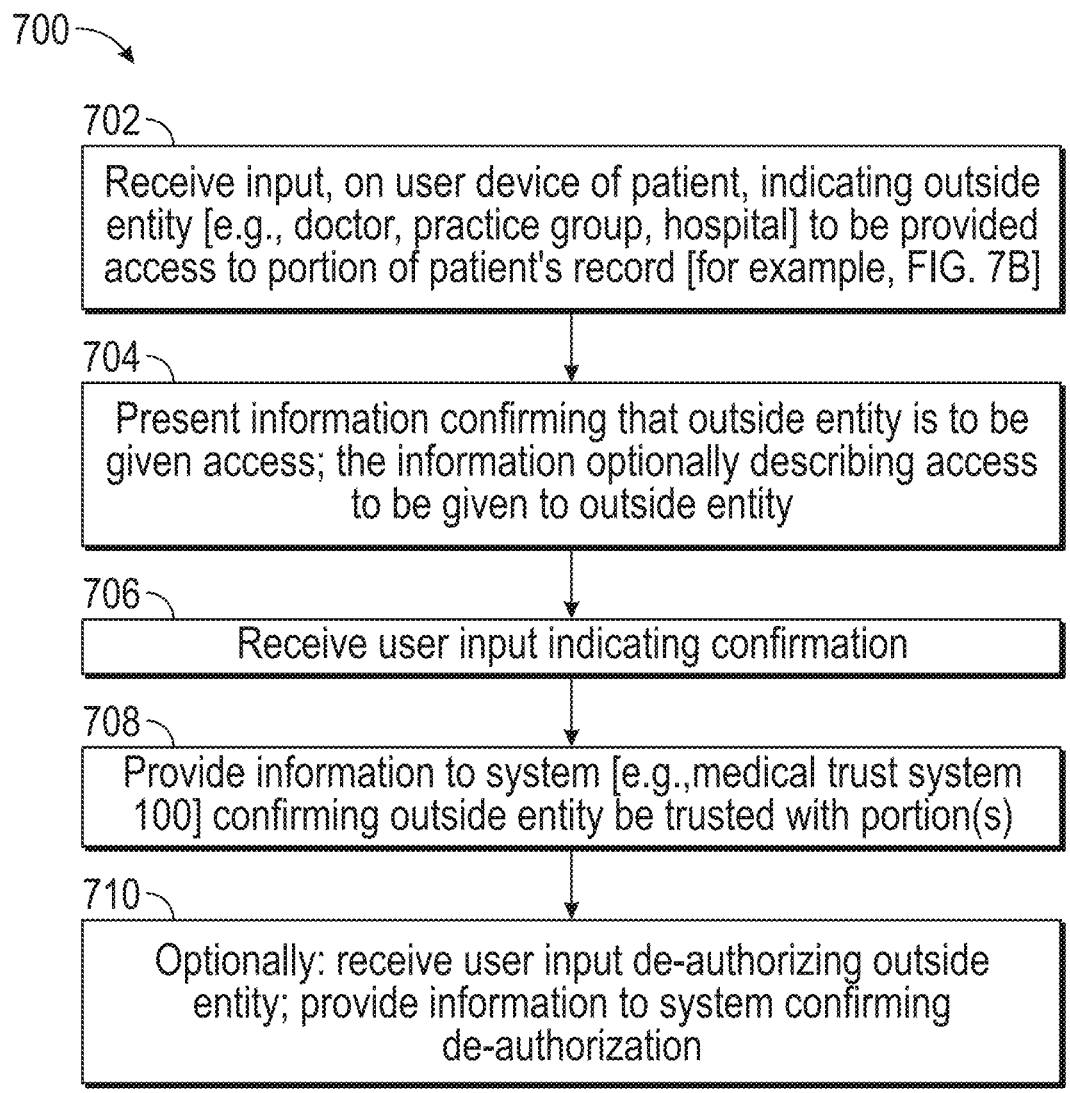
FIG. 7A is a flowchart of an example process for a patient indicating trust to an outside entity.

FIG. 7A is a flowchart of an example process for a patient indicating trust to an outside entity. For convenience, the process 700 will be described as being performed by a user device of one or more processors.

The user device receives input from a patient indicating an outside entity to be trusted with portion(s) of the patient's health record (block 702). As will be described below, with respect to FIG. 7B, a patient can utilize his/her user device to indicate trust to an outside entity. For example, the patient can indicate trust while being located at the offices, or a work place, of the outside entity.

The patient can utilize an application executing on the user device to initially provide authentication information to the system. The system can then authenticate the patient. The system can obtain an indication of a health record associated with the patient, and enable the patient to trust outside entities. As an example, the patient can walk into offices of a particular outside entity and provide information to the application identifying the outside entity. For example, the patient can provide a name of the outside entity or the user device can obtain an identification of the outside entity from a location of the user device. The system can then obtain an identification of the outside entity, and update the user account information with trust indicated by the patient. An example of obtaining an identification can include obtaining user account information.

Figure 7B:
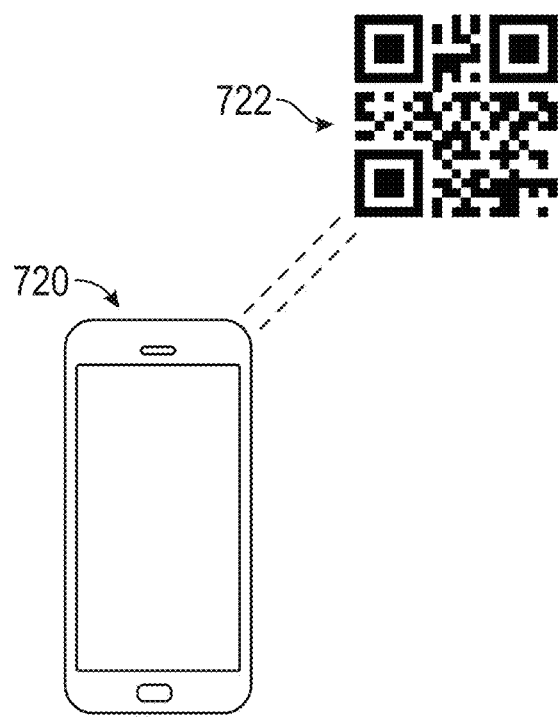
FIG. 7B is a block diagram of an example embodiment of a patient indicating trust to an outside entity.

The user device presents information confirming trust is to be given to the outside entity (block 704). As illustrated in FIG. 7B, the user device of the patient can present information (for example, user interface elements) to confirm the trust. For example, the user device can present user interface elements. As described above, the patient can indicate selected portions of his/her health record that are to be trusted with the outside entity. Optionally, the outside entity can have an associated trust policy, and the patient can review the trust policy and/or optionally confirm the trust policy. For example, the user device can present a visual representation of the patient's medical record along with a visual representation of the trust policy. The user device can present the health record, and selections of portions of the health record that would be shared with the outside entity. The patient can then confirm that the trust policy is acceptable, and indicate trust to the outside entity. The system can, in addition or alternatively, indicate portions of the patient's health record that are to be trusted with the outside entity, and the patient can confirm. For example, the system can monitor portions of health records that are requested by outside entities, according to a type of the outside entity. An example type can include a role of the outside entity such as a type of doctor. The system can then determine portions that are commonly requested by a type of the outside entity and which are subsequently accepted by patients. Furthermore, in an example where the outside entity requests portions of the patient's health record, the user device can present information indicating a frequency or commonality with which the requested portions are requested by other outside entities. For example, the user device can indicate that for a first portion, a particular percentage of other outside entities request the same first portion. This percentage can be of the same type of doctor and/or across all care provider accessors.

The user device receives user input indicating confirmation of the trust (block 706). As illustrated in FIG. 7B, the user device can request confirmation that the patient is to provide trust to the outside entity. Optionally, the patient can indicate that the trust is to be temporary, for example if the patient is visiting the outside entity as a second opinion or for a quick visit and does not intend to retain the outside entity for additional medical care. The temporary trust can indicate, to the system, that the trust is to be provided for a particular period of time (for example, a present day, a subsequent week). The temporary trust can indicate that the trust is to be provided for a number of accesses to the patient's health record (for example, a present access, one or more subsequent accesses, and so on). If the outside entity requires additional time, or accesses, the system can notify the patient of the outside entity's request and the patient can confirm or deny the request. Optionally, and as described below with respect to FIG. 8, the outside entity can retain access rights to the trusted portions up until a time that the outside entity is de-authorized. Subsequently, any updates made to the portions can be inaccessible to the outside entity.

The user device provides information to the system confirming the outside entity is to be trusted (block 708). Upon interacting with his/her user device, the user device provides information to the system confirming trust, and the system updates user account information of the outside entity. For example, the updated user account information can specify a unique identifier associated with the patient's health record or optionally identifiers of trusted portions of the health record. The system can also update the patient's health record to indicate trust to the outside entity.

Optionally, the trust assigned to the outside entity can be further assigned to associated outside entities. For example, the trust assigned to the outside entity can be further assigned to other medical professionals associated with the trusted outside entity. As an example, doctors within a same practice group can be assigned trust. Additionally, the trust can be assigned to departments associated with the outside entity, for example a billing department can obtain an indication of trust. The billing department can have access to the same, or lesser, portions of the health record, or access to summary information, such as access to billing codes provided by medical professionals. Optionally, the system can automatically reformat doctor-inputted information, such as billing information, into a different format. For instance, a format can be a particular insurance format, billing format, and so on.

The user device optionally receives input de-authorizing the outside entity, and provides information to system confirming loss of trust to the outside entity (block 710). As described above, patients can indicate that outside entities, such as medical professionals, are not to be trusted anymore. As an example, the patient may change doctors or care providers. The user device can optionally remind patients that they may wish to de-authorize outside entities. For example, the system can determine that a patient has seen an outside entity associated with a same type as an earlier trusted outside entity greater than a threshold rate. The system can determine that the patient has only seen a new outside entity within a threshold period of time, and hasn't seen a different outside entity associated with the same type within the threshold period of time. This may indicate that the patient is seeing a new doctor instead of an old doctor. The system can then provide information to the user device prompting the patient to confirm whether trust is to be de-authorized. For example, the user device can state, "You haven't seen [Dr] in a while, are you still a patient of that [Dr]?" The system, upon receiving conformation that the outside entity is to be de-authorized, can update the user account information of the outside entity, the trusted portions of the health record, and so on.

In this way, the outside entity will be unable to access additional information included in the previously trusted portions of the health record. Furthermore, when the outside entity attempts to access the patient's health record, the outside entity's user device can present information indicating a loss of trust, and can optionally block the outside entity from accessing the previously trusted portions.

FIG. 7B is a block diagram of an example embodiment of a patient indicating trust to an outside entity. The illustration of FIG. 7B includes an example user device 720 being operated by the patient. The patient can walk into the offices, work area, and so on, of an outside entity, such as a doctor in this example, and can utilize the user device 720 to indicate trust to the doctor.

In the example of FIG. 7B, the doctor's office or a front area of the doctor's office can include a visual identifier 722 associated with the doctor or practice group. For example, the visual identifier 722 can be a QR code. As another example, the visual identifier 722 can be a bar code, text, a value, and so on. Utilizing the user device 720, the patient can scan the visual identifier 722 (for example, obtain one or more images of the visual identifier 722), and the user device 720 can obtain identification information associated with the doctor. In this way, the patient can easily obtain an indication of the doctor and/or practice group at which they are located. Optionally, the patient can specify a particular name of the doctor and/or practice group and the user device can provide the specification to the system (for example, the medical trust system 100). The system can then obtain an identification of the specified name, and provide information to the user device associated with the name. This can include an icon or logo of the doctor or practice group, a full name, address, and so on. In this way, the patient can receive confirmation that the name was specified correctly.

The patient can then confirm trust is to be given to the doctor 726 and/or practice group 724. For example, the visual identifier 722 may identify a name of a practice group and the patient can indicate trust is to be provided to the healthcare provider 724 via user interface elements present on the patient's user device 720. Through the trust provided to the practice group, the doctor the patient is seeing can be provided trust. Optionally the patient can receive information identifying that all doctors or all doctors of a particular type are to be given trust. Optionally, the patient can further utilize the user device 720 to specifically indicate trust is to be given to the particular doctor 726 the patient is seeing.

The user device 720 can indicate that particular departments are to be provided access to portions of the patient's health record, such as the billing department, scheduling department, and so on. For example, and with reference to FIG. 2, a portion 220 of the patient's health record may be associated with scheduling and the scheduling department can be provided access to the scheduling portion 220. In this way, upcoming appointments can be included in the patient's health record, and made accessible via an application executing on the user device 720. Optionally, the appointments can be further trusted to outside applications, such as calendar applications, which can automatically obtain new appointments and update calendar applications utilized by the patient. Similarly, the billing department may be trusted with particular types of information provided by the doctor, such as billing codes, summary information, and so on.

To increase security, the user device or system, can ensure that the patient's user device is located within a threshold distance from a location of the practice group. For example, the user device can obtain GNSS or GPS information or rough location information based on cell-service triangulation. An IP address can also be utilized to indicate location, for example if the patient is connected via a WiFi network. The user device or system can utilize the location information to ensure that the patient is located proximate to the practice group. Optionally, the patient can indicate trust to the practice group and/or doctor while located away from the location of the practice group.

The patient may also provide a QR code, or other visual identifier, and the doctor 726 can similarly scan the QR code. For example, optionally the doctor 726 may be required to confirm an identity of the patient. The doctor 726 can scan the QR code, and indicate trust is to be provided to the patient. The medical trust system 100 may then store information associated with the trust, and allow the patient to access portions of his/her health record that are related to the doctor 726.

Furthermore, a QR code can be placed at a pharmacy, and through scanning of the QR code via a user device, a patient can indicate trust to the pharmacy. The pharmacy can then access a portion of the patient's health record associated with prescriptions, and can prepare prescriptions for the patient. For example, the pharmacy can prepare the prescription without a physical note from the doctor. Since the portion of the patient's health record associated with prescriptions can include information from trusted medical professionals, who can similarly be identified and ensured to be trustable by the system 100, the pharmacy can have knowledge that the prescriptions are real. As an example, a prescription may indicate a particular medical professional that specified the prescription, and the medical trust system 100 can indicate the trust between the medical professional and the patient. The pharmacy's access to this prescription information can therefore greatly simplify the process by which prescriptions are provided to patients. Furthermore, since the patient is operating his/her user device, an identity of the patient can be confirmed. That is, as described above the health communication protocol can ensure that only an authorized user of an authorized user device can access the user's health record. For example, authentication or biometric information of the patient can be confirmed, identification information of the user device can be confirmed, and so on. In this way, based on the patient indicating trust to the pharmacy, for example trust of the prescription information in his/her health record, the pharmacy can provide a prescription to the patient.

Figure 8:
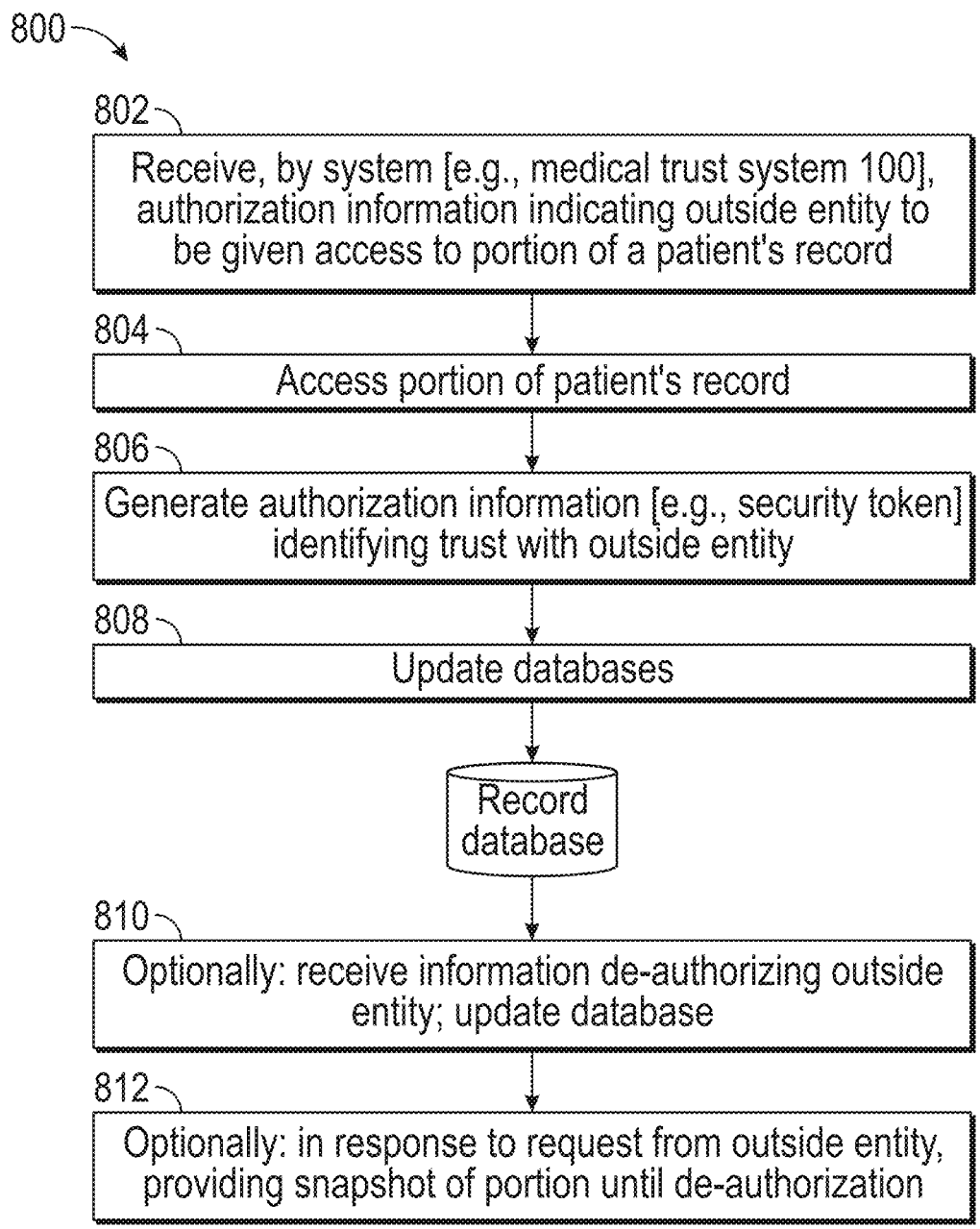
FIG. 8 is a flowchart of an example process for authorizing an outside entity to access a health record.

FIG. 8 is a flowchart of an example process 800 for authorizing an outside entity to access a health record. The process 800 can be performed by a system of one or more computers.

The system receives authorization information (block 802), accesses a portion of patient's record (block 804), generates authorization information (806), and updates one or more databases to indicate that a patient trusts the outside entity (block 808). As described above, with respect to FIGS. 7A-7B, a patient can indicate trust to an outside entity, and the system can maintain information identifying the trust.

The system optionally receives information de-authorizing the outside entity, and updates the database (block 810). As described above, with respect to FIG. 7A, patients can revoke trust to outside entities, and the system can cause the trust to be severed.

The system optionally generates a snapshot of trusted portions until de-authorization by the patient (block 812). As described above, optionally outside entities can retain access to previously trusted portions. For example, the previously trusted portions can be utilized to retain records for recording a minimum duty of care was provided, for insurance purposes, and so on. The system can maintain information identifying a time at which the outside entity was de-authorized, and for subsequent requests, can generate a snapshot of the patient's health record as it existed at the time. For example, the system can monitor changes to each patient's health record and record time stamp information or information identifying the changes.

Figure 9:
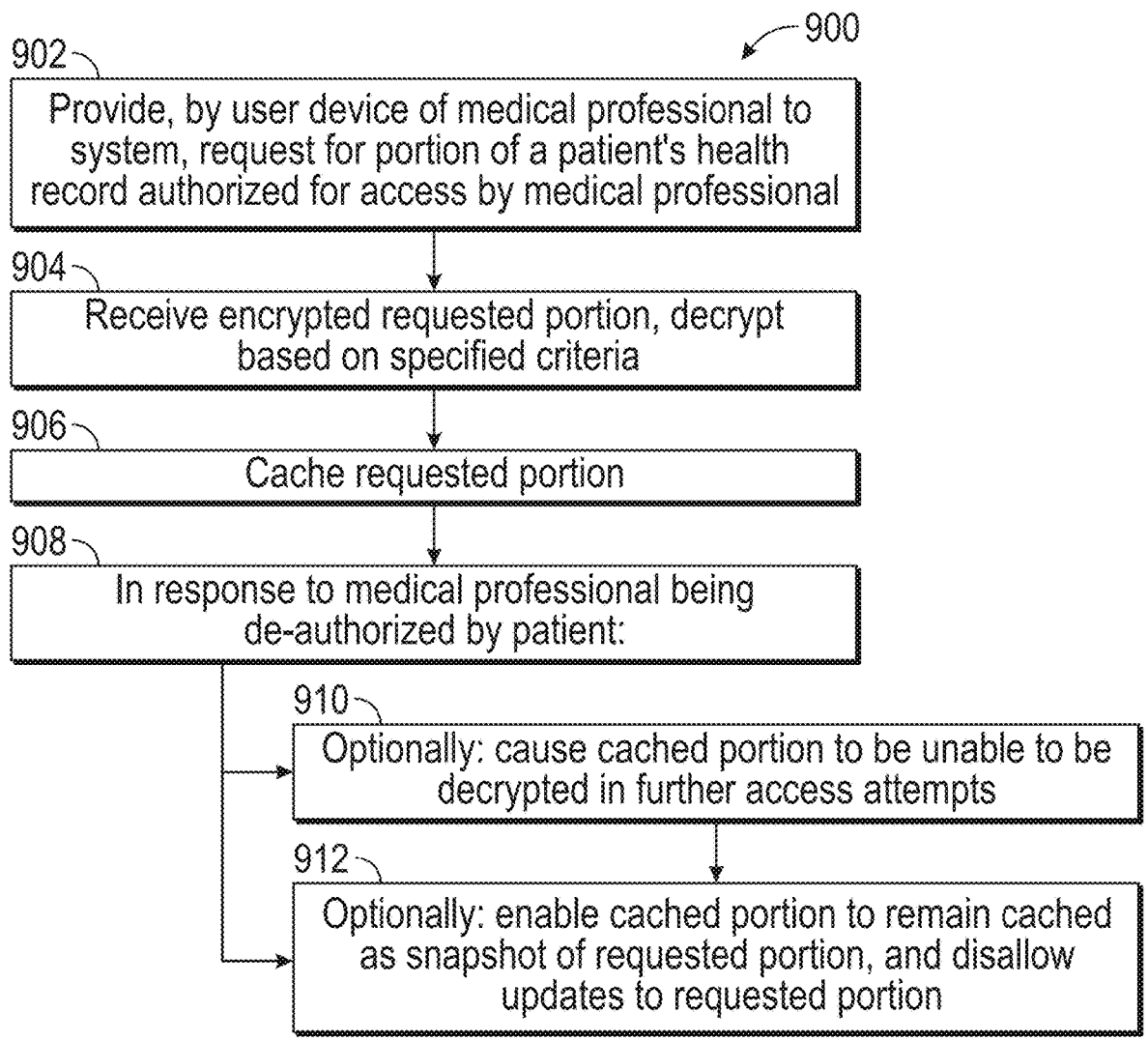
FIG. 9 is a flowchart of an example process for caching of a portion of a health record.

FIG. 9 is a flowchart of an example process 900 for caching of a portion of a health record. The process 900 can be performed by a system of one or more computers in combination with a user device of one or more processors.

The user device provides a request for access to a patient health record trusted to an outside entity utilizing the user device (block 902). The outside entity, for example a doctor, can utilize his/her user device to request portions of the patient health record, and the system can provide access to the portions.

The user device receives the requested portion (block 904). The system can provide an encrypted version of the requested portion, for example via the health communication protocol described above, and the user device can decrypt the requested portion.

The user device caches the requested portion (block 906). The user device can optionally cache the requested medical information, such that the medical information can be accessed without requiring additional network calls to the system. Optionally, the system can indicate whether the requested portion can be cached. As an example, the system can indicate that a mobile device is unable to cache portions that include large images (for example, DICOM image data), while other user devices can cache such portions. Additionally, the system can indicate that the cached information is able to be accessed for a certain period of time, or a certain number of accesses, and if the limits are exceeded, the user device is to provide a subsequent request for access.

The outside entity can update the cached portions or include additional information in the cached portions. For example, a doctor can obtain medical images of the patient, and include the medical images in a cached portion. The cached portions can subsequently be synced with the system. For example, the system can indicate that after a threshold amount of time, the cached information be updated with the system. In this way, the system can maintain fresh versions of the information. Additionally, particular systems can function as the owner of the information, such that the health record is de-centralized. In this scenario, the system can enable particular user devices of the outside entity (for example, server systems), to maintain health record information and the system can provide access to the health record information via the server systems of the outside entity.

The system can de-authorizing an outside entity (block 908). As described above, patients can indicate a loss of trust with respect to outside entities.

Optionally, the system, or user device, causes the cached portion to be unable to be accessed by the outside entity or cleared (block 910). Upon a loss of trust, the outside entity's user device can block access to the cached portion. For example, the user device can request updated trust information from the system and upon determining that the outside entity is no longer trusted with the patient's health record, the user device can be unable to decrypt the cached portion.

Optionally, the cached portion can be retained as a snapshot of the portion until the loss of trust (block 912). The cached portion can remain on the user device, but updates to the cached portion can be blocked by the system. For example, upon a severing of trust, the cached portions can be retained.

Figure 10:
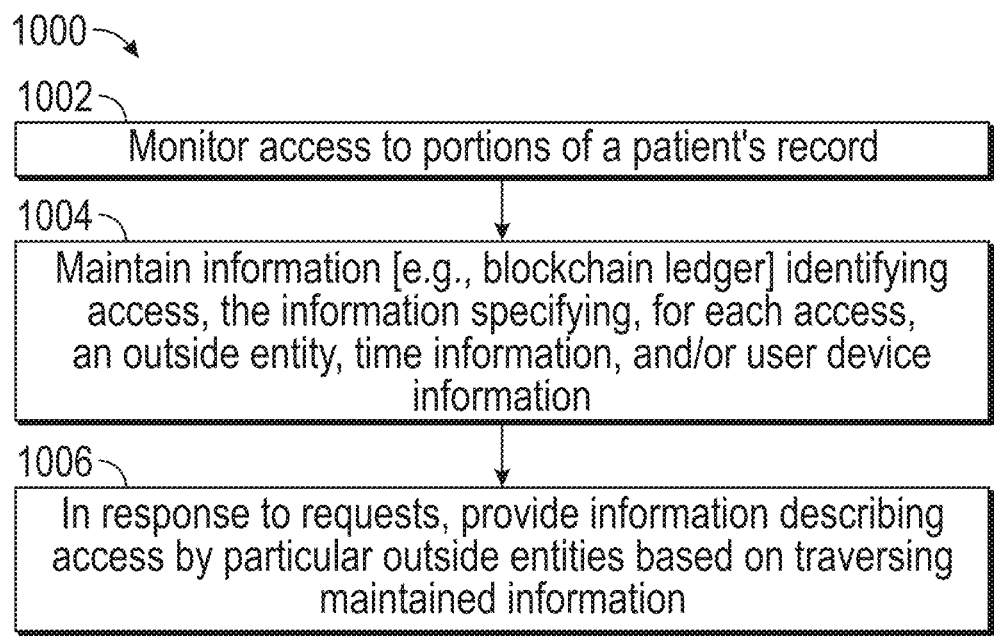
FIG. 10 is a flowchart of an example process for recording access information associated with health records.

FIG. 10 is a flowchart of an example process 1000 for recording access information associated with health records. The process 1000 can be performed by a system of one or more computers.

The system monitors access to a patient's health record (block 1002). The system monitors access by outside entities. For example, the system can maintain information identifying who accessed each portion. The system can also maintain information identifying when each portion was accessed. The system can also maintain information identifying where each portion was accessed (for example, the system can monitor user devices, including locations of each user device, used to access each portion).

The system maintains information identifying the access (block 1004). As described above, the system can monitor accesses to portions of the health record. Optionally, the system can maintain the information as a blockchain. For example, this can be a ledger identifying records of access connected via encrypted information.

The system provides information describing access (block 1006). The system can receive a request for access attempts. For example, an outside entity may wish to view his/her accesses. As another example, an insurance company may wish for proof that portions were accessed by outside entities. The system can traverse the blockchain and identify accesses, updates, or changes, to particular portions, and provide summary information to the requesting outside entity.

Additionally, the blockchain may be store trust information. For example, as a patient trusts new medical professionals, the blockchain can be updated to record the trust. As another example, as the patient indicates that a medical professional is not trusted, the blockchain can be updated to record the loss of trust. In this way, to determine whether a medical professional is trusted, the system can traverse the blockchain. For example, the patient may be associated with a unique identifier. The system can traverse the blockchain for updates associated with the unique identifier, and determine whether a particular medical professional (e.g., associated with an identifier) has been trusted by the patient.

FIG. 11 includes example user interfaces presented on a user device 1100. The user interfaces are example of user interfaces generated by an application executing on the user device, or examples of user interfaces associated with a web application running in a browser on the user device 1100. As an example, the application may be in communication with a software agent executing on the user device. The software agent may route information from the application to the medical trust system 100 (FIG. 1). Additionally, the software agent may route information from the medical trust system 100 to the application.

As described above, the system (for example, medical trust system 100) can analyze medical information of patients, and can provide information related to particular diseases, ailments, and so on, of the patients. For example, and with respect to FIG. 2, the system can access information included in a personal medical record portion 216 of a patient's health record 212, and can parse the information to determine information to recommend to the patient. Since the personal medical portion 216 can be separated from a portion 214 that includes personally identifiable information, the system can determine diseases, and so on, of patients without having access to the patients' names, addresses, social security numbers, and so on. The system can then present information, such as information further detailing any diseases, possible questions to ask doctors, and so on.

Additionally, the system can recommend clinical trials that a patient can join. As illustrated in FIG. 11, the system has determined that the patient is suffering from "Multiple Myeloma" 1102, and indicates that the patient can join particular clinical trials related to "Multiple Myeloma" 1102. For example, user interface 1104 indicates several clinical trials and further indicates that the patient can read more about each. As illustrated, the patient has selected a particular clinical trial 1106, and the user device 110 is presenting information related to the clinical trial 1106. The presented information can include a description, overview, and/or eligibility information, of the clinical trial 1106.

Optionally, the system can maintain metadata associated with patients (for example, metadata with personally identifiable information removed), and clinical researchers can review the metadata to identify patients that are matches for clinical trials. The clinical researchers can then provide information to the system, and the system can present information identifying the clinical trial to the patient through, for example, user interface 1106.

The application executing on the user device 1100 can be a third-party application, and can be in communication with the medical trust system 100. For example, the application can provide requests to the system 100, and the system 100 can respond to the requests. That is, the system 100 can function as a routing of information and the application itself may parse the information and determine clinical trials for recommendation.

The patient utilizing the user device 1100 can indicate that he/she is interested in joining the clinical trial, and can indicate trust is to be provided to the clinical researchers. For example, particular clinical researchers may be interested in merely having access to medical information of the patient for a clinical trial and the patient can indicate that trust is to be provided to the clinical researchers for such access. Other clinical researchers may be interested in the patient performing actions, such as trying procedures, drugs and so on, and the patient can indicate trust to these clinical researchers.

Through use of metadata, clinical researchers can further determine an extent to which particular diseases occur. That is, the clinical researchers can be provide queries to the system identifying particular diseases and the system can obtain a frequency of occurrence or a total occurrence. The clinical researchers can further refine the search through other features described in health records, for instance an age range, lifestyle habits, and so on.

Uniqueness of Patient/Identity of Patient

Using the techniques described herein, access to personally identifiable information of a patient can be separated from medical information of the patient. In this way, the patient can indicate his/her identity in particular situations, while in other situations can provide relevant medical information without identification. Additionally, in particular situations the patient may initially indicate identity, and then subsequent interactions his/her identity can be private. Therefore, and as will be described, a uniqueness of the patient can be separated from a particular identity of the patient.

As described above, with respect to at least FIGS. 2 and 6, a patient can access his/her medical records through communications with the medical trust system 100 described above. For example, FIG. 2 illustrates a patient responding to requests for information 206 to prove his/her identity, and based on the responses the medical trust system 100 can provide access. In this way, the patient's responses to questions directed to unique features of his/her life can ensure that the patient is the person associated with the medical records. Furthermore, and as described above, a medical professional can confirm the patient's identity prior to access being granted by the medical trust system 100.

Based on being positively identified, the medical trust system 100 can provide one or more certificates for local storage on the patient's user device. A certificate can provide an ongoing validation that an operator of the user device is associated with particular medical records. Therefore, the certificate can represent an authorized token associated with an identity of the operator of the user device. However, the certificate may not itself be directly associated with personal information of the operator. That is, the authorized token enables access to the personally identifiable information, but the token itself does not identify a name of the patient.

The certificate can therefore represent several things with respect to the techniques described herein. As an example, a user device holding a certificate can provide an indication that an operator of the user device has an associated unique medical record. Therefore, the certificate indicates that the operator has unique features described in his/her medical record. As another example, the certificate can be utilized to provide identifying information of the operator, for example a name, address, phone number, and so on. The distinction between being a unique person (e.g., having a unique medical record), and an identifiable person, can be utilized to different effects according to use case.

As an example, a medical professional may require particular information about the patient, but may not need to know his/her personally identifiable information. In this example, the patient can provide trust to the medical professional with respect to unique features of his/her medical record. However, the patient can elect not to provide personally identifiable information. In other use cases, confirmation of an identity of the patient may be required. For example, confirmation of the identity may be required prior to a drug test being performed on the patient.

As a further example, if the patient is getting a routine shot, the person giving the shot may not require the patient's personally identifiable information. However, unique features associated with the patient, such as allergy information, history of recent shots, and so on, may be required. Therefore, as the patient interacts with the medical professional, the user device of the patient can provide confirmation of the patient's uniqueness to a user device or system of the medical professional. For example, based on near field communications (NFC), the user device can provide information associated with the certificate to the user device or system of the medical professional. The information can include a sub certificate generated from the certificate received from the medical trust system 100 (e.g., a root certificate). The information can optionally include particular features of the patient, such as allergies as described above. This information can be signed via the certificate or sub-certificate, such that the information can be guaranteed to be accurately associated with the patient. Optionally, the patient can indicate trust of portions of his/her medical records to the medical professional, and the medical professional can access the portions according to the techniques described herein.

Similarly, if the patient's identity needs to be confirmed, the patient's user device can provide information confirming personally identifiable information of the patient. For example, the information can include a sub certificate, and the personally identifiable information can include a name, phone number, and so on.

With respect to the below-described example of FIG. 12 in which a patient is undergoing a medical procedure, the patient's identity may be required to be confirmed. For example, the patient may be having his/her bloodwork done, blood pressure taken, or be undergoing a drug test. Prior to initiation of the medical procedure, the patient can confirm that his/her identity corresponds to a person scheduled to undergo the medical procedure. While the patient can optionally verify identity based on government issued identification cards (e.g., a driver's license), the techniques described herein enable rapid identification.

For example, as the patient walks up to a front desk of a hospital or medical practice group, the user device can provide confirmation of uniqueness of the patient to systems at the front desk. As described above, the uniqueness can be determined based on a certificate or authorization token stored by the user device. The information provided to the front desk systems can therefore indicate an associated medical record, such as a reference to the patient's medical record. The user device may optionally automatically provide information, or provide information in response to the patient's interaction with the user device. For example, the user device can access calendar information associated with the patient and identify the medical procedure. The user device can then monitor its location, and if the location corresponds to a location associated with the medical procedure, the user device can provide the information to the front desk systems. Optionally, the user device can provide the information if the front desk systems had previously been trusted by the patient.

Based on the received information, the systems at the front desk can check-in the patient. For example, if the patient has previously trusted the systems or the front desk department, the systems can access scheduling information included in the patient's medical record. However, the systems may not have access to a name of the patient, just the scheduling information. Therefore, while the systems can access this portion of the medical record, the systems will not have knowledge of personally identifiable information. Based on this level of access, the systems can identify the appointment in the scheduling information. As described above, with respect to FIG. 7B, the front desk systems may automatically place upcoming appointments in the patient's medical records. Therefore, upon detection of a present appointment, the systems can check-in the patient. In this way, the patient's privacy can be better ensured, such that the front desk workers may not have access to personally identifiable information.

Indeed, the interaction can be automatic. For example, the patient's user device can automatically communicate with the front desk systems, as described above. The front deck systems can then automatically check the patient in, and optionally alert a medical professional of the appointment. Optionally, the user device of the patient can present an acknowledgement that he/she is checked in. Furthermore, all questionnaires, insurance information, and so on, may automatically be handled according to the techniques described herein. For example, the front desk systems can access insurance information of the patient as indicated in his/her medical record. Additionally, the patient can avoid filling out questionnaires requesting routine medical information. That is, a medical professional about to see the patient can access the patient's medical record, and view the routine medical information. As will be described below, with respect to FIGS. 14-15, the medical professional can utilize a user interface to present medical information of patients. Optionally, upon an upcoming appointment of the medical professional, the user interface utilized by the medical professional can automatically present the routine information of the patient as obtained from his/her medical record. Additionally, when seeing a new medical professional, the patient can indicate trust to the medical professional according to the techniques described herein. The new medical professional can then view the routine information, and optionally request additional information from the patient that can be included in the patient's medical record.

However, as the patient undergoes the medical procedure, the patient's identity may be required to be confirmed. Similar to the above, the patient's user device can provide confirmation of the patient's identity to the medical professional.

Figure 12:
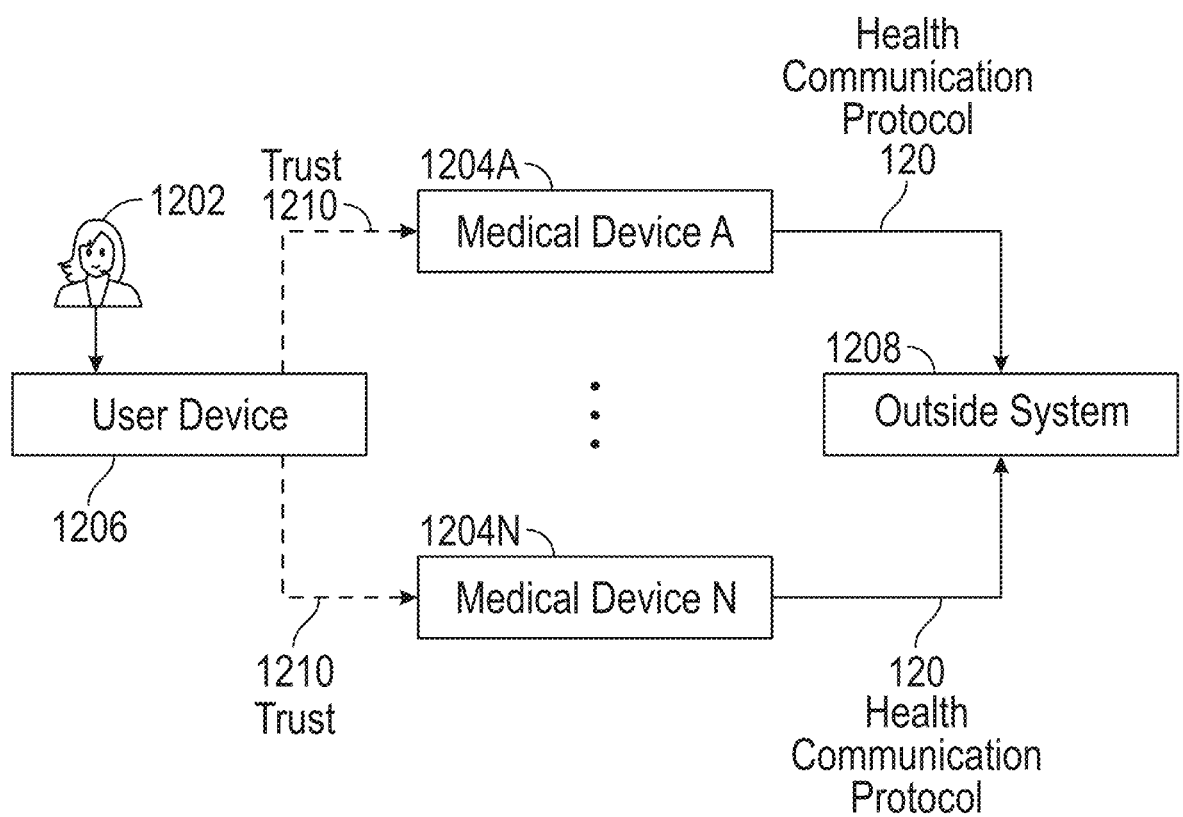
FIG. 12 illustrates an example of trust being associated with devices of outside entities.

FIG. 12 illustrates an example of trust being associated with devices of outside entities. For example, devices can include medical equipment utilized during performance of medical procedures. Devices can further include medical equipment utilized to obtain medical information associated with a patient 1202. The devices can be connected to one or more networks, for example internet-of-things devices each associated with an address. For example, an address can be an IPv6 address. As will be described, an entire chain of devices, systems, user devices, and so on, that are utilized during performance of a medical procedure can be secured. To secure the devices, the devices can be required to be trusted by a patient undergoing a procedure. That is, the devices can be required to be authorized to store medical information associated with the patient. In this way, privacy associated with medical information can be strictly enforced.

As an example, a patient 1202 may be undergoing a blood pressure test. To ensure that blood pressure devices store medical information of the patient in accordance with the techniques described herein, the patient 1202 can indicate trust to the blood pressure devices. Each blood pressure device can therefore strictly enforce constraints associated with handling, and/or access of, medical information of the patient 1202. As described above, with respect to at least FIG. 1, a health communication protocol 120 can be used to provide data 126 between systems, devices, and so on. In this example, a blood pressure device can obtain medical information of the patient 1202, and the obtained medical information can be encrypted. Thereafter, to obtain the medical information for storage on an outside system, the outside system can be required to receive the medical information via the health communication protocol 120. For example, the outside system may be a system associated with a third-party medical lab company, a system associated with a medical professional performing the blood pressure test, and so on. In this way, all devices, systems, and so on, can ensure that access to the medical information is constrained.

As will be described, trust can be provided from a patient 1202 to devices 1204A-1204N via explicit indication of trust, or via one or more trust policies as described above. For example, the patient 1202 can utilize his/her user device 1206 to indicate explicit trust. As another example, the patient 1202 may have previously trusted a medical professional, and based on a trust policy associated with the medical professional, the devices 1204A-1204N can be automatically trusted. In this way, the devices 1204A-1204N can similarly enforce constraints on access to medical information as described herein.

As illustrated in FIG. 12, a patient 1202 is undergoing a medical procedure that includes use of medical devices 1204A-1204N. Example medical devices can include blood pressure devices, x-ray devices, MRI devices, or any arbitrary device that can measure or ascertain information utilized in medical diagnoses. As described above, the medical devices may be connected via one or more networks, such that they can receive and transmit information. Example networks can include local area networks, wide area networks, the internet, and so on. In this way, each device can be associated with a network identifier, such as an internet protocol (IP) address, a media access control (MAC) address, and so on. As will be described below, access to information obtained by the devices 1204A-1204N can be constrained according to the techniques described herein.

To ensure that privacy is strictly enforced, the patient 1202 can indicate trust 1210 to the medical devices 1204A-1204N that will be utilized. For example, and as described above, the patient 1202 can utilize an application on his/her use device 1206 to cause trust to be provided to the medical devices 1204A-1204N. Similarly, according to a trust policy, the patient 1202 may automatically trust the medical devices 1204A-1204N. That is, if the medical devices 1204A-1204N are utilized by a medical professional the patient 1202 trusts, the devices 1204A-1204N may be automatically trusted.

Similarly, the medical devices 1204A-1204N can limit use of the devices by a medical professional until confirmation of the patient's identity has been confirmed. For example, in addition to being trusted by the patient, the medical devices 1204A-1204N may require that the patient's 1202 identity correspond to an identity of a person scheduled for the medical procedure. The certificates described above can be utilized to provide such confirmation, and for example can provided over a near field communication (NFC) or local area network.

As the medical devices 1204A-1204N perform tests, they can store medical information associated with the patient 1202. In accordance with the techniques described herein, this medical information can be encrypted as it's stored. For example, the medical information can be encrypted based on one or more of the certificates or tokens described above. Upon completion of the medical procedure, the medical devices 1204A-1204N can provide the stored medical information to an outside system 1208 for storage. For example, the outside system 1208 can be the medical trust system 100, and the system 100 can update the patient's 1202 medical records. As another example, the outside system 1208 may be a server system associated with a hospital. As described above, the medical trust system 100 may enable communications between the server system and user devices requesting access to the stored medical information. The outside system 1208 can utilize the health communication protocol 120, as described above, to ensure privacy of the medical information. In this way, the medical professional can access the medical information from the medical devices 1204A-1204N based on access to the patient's medical records stored in the medical trust system 100. Optionally, the outside system 1208 can provide the medical information to a system associated with the medical professional via the health communication protocol 120. The medical professional can access the medical information based on satisfying constraints associated with the protocol 120. For example, access can be predicated on the medical professional's identity, system being utilized to access the medical information, and so on as described above.

Figure 13:
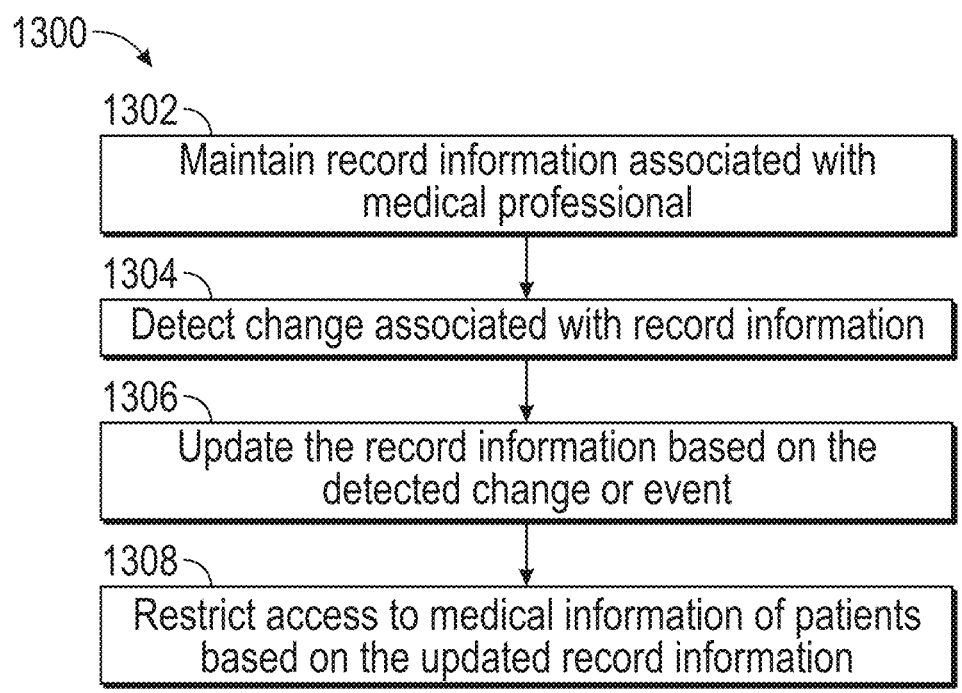
FIG. 13 is an example is a flowchart of an example process for updating access rights associated with a medical professional.

FIG. 13 is an example is a flowchart of an example process 1300 for updating access rights associated with a medical professional. For convenience, the process 1300 will be described as being performed by a system of one or more computers and/or servers, including for example, the medical trust system 100.

As described above, with respect to at least FIG. 3, the system can receive authentication information from medical professionals, and provide authenticate tokens to a user device of the medical professionals. In this way, medical professionals can be authenticated, and access to medical information can be constrained. For example, access can be constrained according to one or more of identification of a medical professional, a user device accessing medical information, and/or time constraints with respect to access. As will be described, the medical professional can automatically be constrained in his/her ability to access medical information. For example, the system can determine that the medical professional is not up to date on certifications, trainings, and so on, and can automatically revoke the ability of the medical professional to access particular medical information.

The system maintains record information associated with medical professionals (block 1302). The system can obtain information associated with medical professionals, for example medical degree information, certifications obtained, trainings performed, and other information relevant to a determination of a medical professional's ability to practice medicine. For example, the system can receive information from the Physician Masterfile, universities, hospitals, and store the information as being associated with the medical professionals.

Additionally, if the universities, hospitals, and so on, issue digital certificates confirming information, the system can store these digital certificates. A particular university may, for example, issue a digital certificate signed by the particular university upon graduation by a medical professional. This digital certificate can therefore provide proof that the medical professional graduated, and can be favored over the medical professional's self-indication of his/her degree. Similarly, continuing medical education (CME) classes can issue similar digital certificates, and the system can obtain these for storage. These digital certificates may have expiration dates associated with them. For example, the continuing medical education digital certificates may have an expiration date associated with one year, two years, and so on, from issuance.

Optionally, if the system does not have access to the above-described digital certificates, the system can ensure that received information is being provided from a trustable entity. That is, the medical professional can indicate trust to outside entities, such as a university, continuing medical education company, and so on. These outside entities can then access the medical professional's record information, and can cause inclusion of information. Similarly, these outside entities may optionally have record information maintained, or accessible by, the system. The system can access this record information and determine whether medical professionals have included records. In this way, the system can have a greater degree of assurance as to the validity of the information.

The system monitors the record information (block 1304). As described above, the system maintains record information associated with medical professionals. The system can monitor the record information, for example periodically, and store information indicating whether the medical professionals are up to date with respect to continuing medical education, trainings, and so on.

The system can monitor the record information to ensure that medical professionals are up to date on required trainings, CMEs, education, and so on. In this way, when the medical professionals receive medical information on their user devices, the system can authorize access to the medical information based on the monitoring. For example, as described above with respect to FIG. 3, the health communication protocol 120 can enforce constraints associated with access of medical information. In addition to constraints on identity of the medical professionals, the system can ensure that the medical professionals are allowed to conduct medicine. The system can maintain rules associated with guidelines of practicing medicine, and can ensure that the medical professionals satisfy the maintained rules, such as trainings, CMEs, and so on.

As an example, a particular medical professional may be required to undergo certification with respect to a particular procedure or use of a particular medical device periodically. Based on monitoring the record information, the system may determine that the medical professional has not undergone certification within the periodic amount of time. The system can therefore block access to medical information of patients that have undergone the particular procedure. Additionally, the system may disallow access to the particular medical device. As described in FIG. 12, medical devices may be associated with the system, such that the medical devices enforce access restrictions based on use of the health communication protocol 120. The system may require that medical professionals authenticate, and based on the authentication, may restrict access to medical devices. Therefore, the system can automatically block access to the particular medical device until receipt of information indicating the particular medical professional has undergone the certification.

The system detects a change associated with monitored record information (block 1306). As described above, the system can monitor the record information, and ensure that medical professionals are allowed to conduct medicine. The system can detect a change associated with the record information of a medical professional. For example, the change can indicate that the medical professional has not satisfied the maintained rules associated with practicing medicine. As an example, the medical professional may need to take a certain number of credits for CME within a certain time period. The system can identify that the certain time period has passed, and may then detect that the medical professional has not taken the certain number of credits. As described below, the system can then restrict access to particular medical information.

The system restricts access to medical information of patients (block 1308). In the example of the medical professional described in block 1306, the system can restrict access to medical information. The nature of the restriction can be based on the detected change.

As an example, if the medical professional is behind on CME credits, the system may provide a buffer period until it restricts access. However, the system may cause the medical professional's user device to present information indicating the CME requirement. For example, when providing medical information to the medical professional via the health communication protocol the system can include information associated with activation of an application on a user device. Optionally, if the medical professional is behind on CME credits, the system can disallow the medical professional from accessing medical information.

As described above, medical professionals can cache medical information on local devices. For example, the local devices can include a server system associated with a hospital, local computers or laptops, and so on. In this case, if the medical professional has access to locally cached medical information, the medical professional may utilize a previously generated token to access the medical information. Therefore, a medical professional may be in violation of the maintained rules, yet still able to access medical information until expiration of the token. The system can therefore remotely cause the disabling of the token. For example, the system can require that when accessing medical information, a user device be required to provide a medical professional's token to the system for continuing validation. In this way, the system can determine that the medical professional is to be disallowed from accessing medical information. Similarly, the system can push information to the local devices indicating that the token is de-authorized. For example, the local device can include computers or laptops known to be utilized by the medical professional, or server systems of hospital or medical groups associated with the medical professional.

User Interface Presentation of Aggregated Information

As described above, the medical trust system 100 can aggregate portions of a patient's medical record that are stored in disparate systems in different locations. That is, a particular hospital may have a portion of the patient's medical record, such as x-rays, while a different hospital may have a different portion. As the patient moves around between hospitals and/or medical groups, the patient's medical record may be separated into chunks of information. The medical trust system 100 can access these different chunks of information, and optionally generate a medical record for presentation on a user device of the patient or a medical professional. As another example, the medical trust system 100 can route information from the disparate systems to the user device. An application executing on the user device can generate the medical record based on the received information.

The medical trust system 100 can index medical information associated with multitudes of patients. When generating a medical record for an example patient, the medical trust system 100 can access systems identified in the index that store medical information of the patient. The medical trust system 100 can then aggregate the medical information, and provide the aggregated information to a user device. Therefore, the medical information obtained represents a current state of the medical record of the patient. That is, since the medical trust system 100 generates the medical record with up-to date information, the medical record is always fresh (e.g., up-to date).

As will be described below, the medical trust system 100 can be utilized to implement electronic health record (EHR)

schemes. That is, any medical information requested by a medical professional or patient can be obtained by the medical trust system 100 in real-time. This obtained information can then be packaged and presented in any form preferred by the medical professional. In contrast to being required to utilize a particular EHR user interface to input and view medical information, the medical trust system 100 can enable any user interface to present medical information. For example, user devices of medical professionals can execute applications, or access web pages, with distinct user interfaces preferred by the medical professionals. The user interfaces, as will be described, can provide requests to the medical trust system 100, and present the received aggregated medical information according to their respective designs.

Given that the medical trust system 100 has access to chunks of medical information associated with patients, complex user queries can be provided to the medical trust system 100 for processing. For example, a medical professional can utilize a user interface to request all MRIs of a particular patient taken during a particular time period. The medical trust system 100 can aggregate all such MRIs, for example from differing hospitals, and provide the aggregated information to the medical professional. Similarly, a patient can utilize a user interface to request summary information associated with his/her medical record. As above, the medical trust system 100 can access differing systems, and aggregate the information into a coherent medical record. In addition, the medical trust system 100, or an application utilized by the patient, can analyze the summary information and determine recommendations for the patient. As an example, and as described in FIG. 11, clinical trials can be recommended to the patient along with their medical record. As another example, support groups for diseases the patient has can be recommended, information related to cohorts of the patient can be provided, and so on.

To ensure privacy of medical information, the medical trust system 100 can enforce the authorization constraints indicated above. For example, the health communication protocol 120 can be utilized, such that a medical professional requesting access to medical information can only access the medical information according to satisfaction of the constraints. Similarly, a patient requesting access to his/her medical information can be required to authenticate, and maintain an authorization token or certificate. For example, the patient may be required to provide factual information, biometric information, and so on, as described above with respect to at least FIG. 2.

Figure 14:
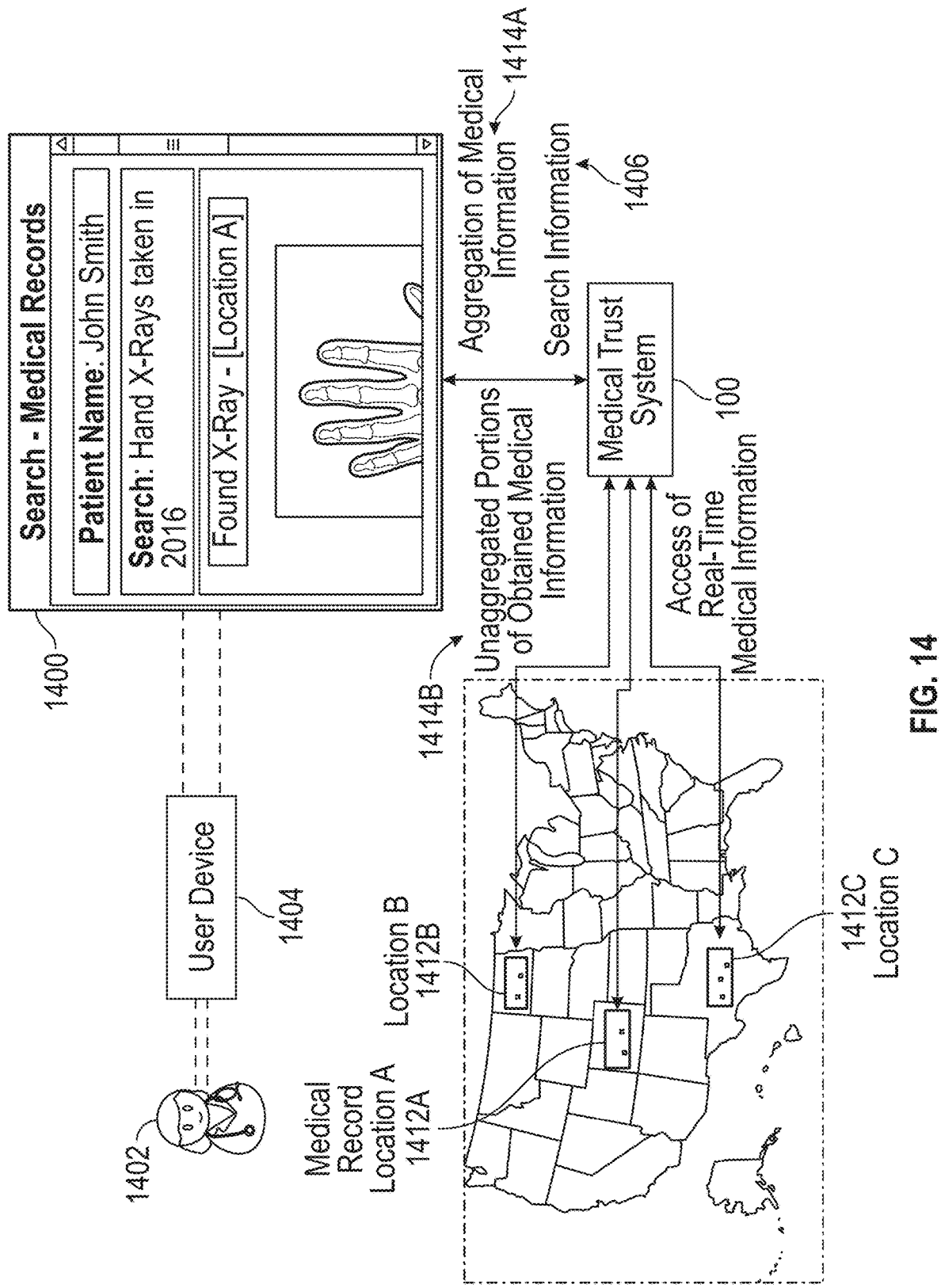
FIG. 14 illustrates an example user interface presenting medical information.

FIG. 14 illustrates an example user interface 1400 presenting medical information. The user interface 1400 can be an example of a user interface 1400 presented via execution of an application executing on a user device 1404 of a user 1402. For example, the user 1402 can be a medical professional or a patient. The application can optionally be an application obtained from an electronic application store (e.g., an 'app'). Additionally, the user interface 1400 can be an interactive document, such as a web page, being served from a system. The user device 1404 can then present (e.g., render) the interactive document for presentation to the user 1402. Optionally, the user device 1404 may be a thin client, and the user interface 1400 may be generated via a back-end web application executing on the system. In this way, the user device 1404 can access medical information utilizing only a web browser. Additionally, the system can receive user interactions with the user interface 1400 and update the user interface 1400 according to the user interactions.

As illustrated, the user interface 1400 can enable access to medical information that has been trusted to the user 1402. For example, the user 1402 can be a medical professional, and the user 1402 can request medical information associated with one or more patients. As described above, the user interface 1400 can be a user interface selected for use by the user 1402. For example, disparate applications can be utilized to present medical information, with the disparate applications providing same, or similar, functionality. The medical trust system 100 can respond to requests from each of the disparate applications, and aggregate medical information in response. Additionally, the user interface 1400 can be customized according to user preferences of the user 1402. For example, the user 1402 can indicate information that he/she prefers be automatically presented upon entering a patient's name.

Similarly, user interfaces can be automatically customized according to user role. As an example, a user interface presented to a surgeon can be different from a user interface presented to a general practitioner. That is, the user interface can present medical information in differing formats, and optionally can automatically request particular types of medical information. As an example, a surgeon can request medical information associated with a particular patient. The user interface can receive aggregated information 1414A from the medical trust system 100, and present a portion of the aggregated information 1414A that is specific to the surgeon. Example information can include recent diet, prior surgeries, and so on. In contrast, a medical practitioner utilizing the user interface may be automatically presented with summary information associated with the patient. Example summary information can include blood pressure, allergy information, recent medical procedures, and so on.

As illustrated, the example user interface 1400 includes a visual portion associated with entry of a patient's name. In this example, the user 1402 can be a medical professional requesting medical information of the patient. For example, "John Smith" has been entered in user interface 1400. The user interface 1400 further includes a visual portion related with entering search terms or queries. The search terms may be provided in terms of natural language search phrases, or optionally as particularly formatted queries connected via logical connections. For example, as illustrated the user 1402 has specified, "hand x-rays taken in 2016." The medical trust system 100 can analyze the search terms and obtain medical information in conformance with the search terms. In another example, queries can be provided, such as "(x-ray type:hand) AND year:2016". This example includes utilization of a logical query schema; however, other types of search terms or parameters may be utilized with the techniques described herein.

Upon entry of a patient's name, and optionally search terms, the user device 1404 can provide the search information 1406 to the medical trust system 100. The medical trust system 100 can analyze the search information 1406, and determine locations at which to access relevant search information. For example, as described above, the medical trust system 100 can index location information associated with the systems that maintain medical information of patients. The index may include particular terms, medical features, and so on, of patients along with corresponding unique identifiers of patients. In this way, the medical trust system 100 can identify, based on the index, network locations at which medical information responsive to a search query is stored. Based on the unique identifiers of patients, the medical trust system 100 can ensure that a requesting user 1402 has been trusted by the corresponding patients to access the medical information. The system 100 can therefore access the index, and provide requests for information to the systems.

Optionally, the medical trust system 100 may index information based on implementation of one or more name services, such as a domain name system. For example, information can be logically classified according to name, such as all medical information related to a patient being indexed under the patient's name. Additionally, specific types of information may be sub-indexed. For example, the system 100 may interpret "johnsmith.xrays" as corresponding to x-rays of patient John Smith. Name records, such as C-NAME records, can therefore be used. Each of the name records may indicate multiple names or addresses associated with a name. For example, johnsmith can be a CNAME record that maps to multiple related name records. To fetch the x-rays from systems, the medical trust system 100 can implement a dynamic DNS that maps particular addresses of systems to associated name. In this example therefore, the medical trust system 100 can provide a request for x-rays of John Smith, and based on the dynamic DNS, can provide requests for information from systems at differing locations 1412A-1412C.

Additionally, as medical information is accessed and updated, the medical trust system 100 can be provided with updates to the medical information. For example, the medical trust system 100 can crawl systems of hospitals and/or medical groups, and maintain index information related to the medical information. The index information can be metadata indicative of types of medical information stored by each system. As described above, the medical trust system 100 can update dynamic DNS records indicating locations at which to find particular information. In this way, as medical professionals see patients, updated medical information, and so on, the medical trust system 100 can update its records indicating locations of the medical information. Therefore, to find all medical information associated with "John Smith," the medical trust system 100 can obtain information indicating locations of systems storing the medical information.

As illustrated, the medical trust system 100 has determined that outside systems in three different locations 1412A-1412C have medical information that satisfies the search information 1406. The medical trust system 100 can communicate with these outside systems via one or more protocols that are specific to the system 100, or specific to the outside systems. For example, particular application programming interface (API) calls may be provided by the system 100 to the outside systems, and the outside systems 100 can respond with the requested medical information. The medical trust system 100 can communicate with the outside systems via the health communication protocol 120, such that privacy is strictly enforced.

Optionally, the medical trust system 100 may have access to cached medical information, which it can directly utilize when responding to the request for search information 1406. For example, the system 100 can cache information to ensure continuity of information, and to reduce access times when requesting information. When responding to a request for search information 1406, the medical trust system 100 can access the cache for utilization when responding. However, since the information in the cache may be out of date, the medical trust system 100 can provide requests to outside systems indicating whether updates have been made to the cached medical information. Specifically, and with respect to the example of FIG. 14, the medical trust system 100 can request whether any updates have been made to hand x-rays of John Smith. The request can be provided to outside systems that store the x-rays. If there are updates, the medical trust system 100 can request the updates for storage.

As described above, for example with respect to FIG. 4, the medical trust system 100 can maintain medical information in one or more databases. For example, particular hospitals and/or practice groups can utilize the databases to store medical information. In this way, the particular hospitals and/or practice groups can utilize the system 100 as cloud storage, in lieu of maintaining their own server systems. In this example, the medical trust system 100 can immediately access the maintained information, without providing requests to outside systems.

Optionally, in contrast to the medical trust system 100 aggregating medical information 1414A, the medical trust system 100 can obtain medical information from systems in different locations 1412A-1412C, and provide the obtained medical information 1414B to the user device 1404. The user device 1404 can then aggregate the medical information, and present the aggregated medical information in user interface 1400.

The medical trust system can therefore obtain medical information based on the search information 1406, and aggregate the medical information to be provided to the user device 1404. As illustrated in FIG. 14, an example x-ray of the hand of John Smith is presented in the user interface 1400.

In addition to requesting information, the user interface 1400 can optionally be utilized to update or include new medical information in a patient medical record. For example, the user 1402 can view the received x-ray, and include notes, annotations, markings, and so on, with respect to the x-ray. The system 100 can store this information for later access by the user 1402, or by other users. For example, other medical professionals who have been trusted to view x-rays of John Smith can view the updated or newly included medical information.

Figure 15:
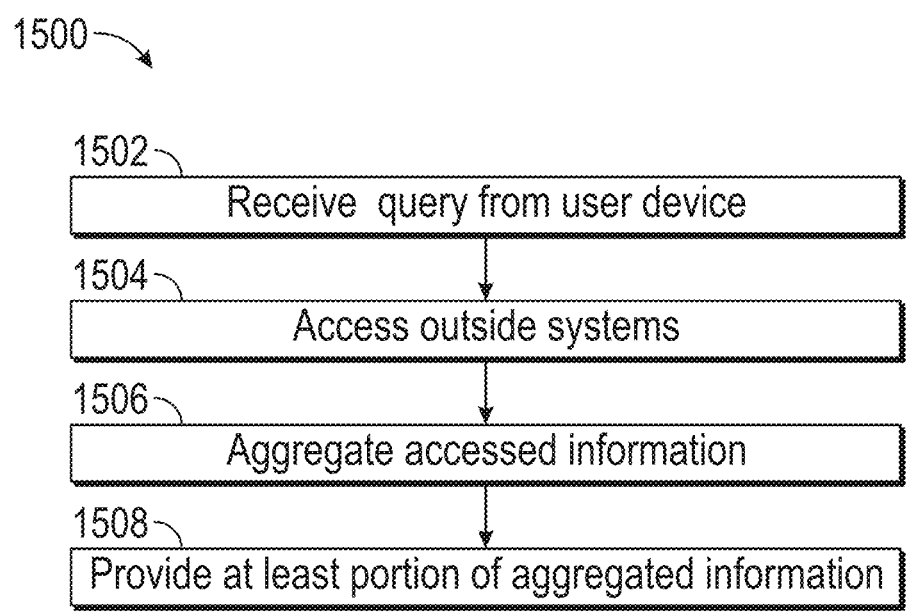
FIG. 15 is an example process of a process for providing aggregated medical information on a user device.

FIG. 15 is an example process of a process 1500 for providing aggregated medical information on a user device. For convenience, the process 1500 will be described as being performed by a system of one or more computers, for example the medical trust system 100.

The system receives a query from a user device (block 1502). The system can respond to queries for medical information from user devices. For example, a patient utilizing a user device may provide a query for his/her medical record. As another example, and which is illustrated in FIG. 14, a medical professional can provide a query for medical information associated with a patient.

The system accesses outside systems (block 1504). The system can analyze the received query, and determine medical information that is to be obtained. For example, the system can utilize natural language processing techniques to identify information being requested by the user device. As described above, medical information may be spread around differing outside systems, such as outside systems of hospitals and/or practice groups.

The system can determine locations at which the requested information is located, and access the outside systems. As described above, the system can maintain metadata indicating features of medical information of each patient. In addition, the system can maintain location information associated storing the features. In this way, the system can utilize the information identified from the received query to identify locations at which the information is being stored.

The system aggregates the accessed medical information (block 1506). The system can obtain medical information from the accessed outside systems, for example using the health communication protocol, and aggregate it. As described above, with respect to FIG. 2, the aggregation can include generating a coherent medical record from the chunks of information obtained from the outside systems.

Optionally, if the query was received from a patient, the system can analyze the aggregated information and determine recommended services, events, and so on, to provide to the patient. For example, and with respect to FIG. 11, the system can identify clinical trials that may be of interest to the patient. As another example, the system can identify offers available to the patient, such as discounts on fitness centers, and so on.

Optionally, the system can provide the obtained medical information to the user device of the patient without aggregating the medical information. Instead, the user device of the patient can aggregate the information for presentation to the user.

The system provides at least a portion of the aggregated information to the user device (block 1508). Subsequent to aggregating the information, for example aggregating chunks of information, the system can provide the information to the user device. As illustrated in FIG. 14, the user device can present the received information via a user interface.

Additional Embodiments

Each of the processes, methods, and algorithms described in the preceding sections may be embodied in, and fully or partially automated by, code modules executed by one or more computer systems or computer processors comprising computer hardware. The code modules (or "engines") may be stored on any type of, one or more, non-transitory computer-readable media (e.g., a computer storage product) or computer storage devices, such as hard drives, solid state memory, optical disc, and/or the like. The processes and algorithms may be implemented partially or wholly in application-specific circuitry. The results of the disclosed processes and process steps may be stored, persistently or otherwise, in any type of non-transitory computer storage such as, for example, volatile or non-volatile storage.

In general, the terms "engine" and "module", as used herein, refer to logic embodied in hardware or firmware, or to a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on one or more computer readable media, such as a compact discs, digital video discs, flash drives, or any other tangible media. Such software code may be stored, partially or fully, on a memory device of the executing computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

User interfaces described herein are optionally presented (and user instructions may be received) via a user computing device using a browser, other network resource viewer, a dedicated application, or otherwise. Various features described or illustrated as being present in different embodiments or user interfaces may be combined into the same embodiment or user interface. Commands and information received from the user may be stored and acted on by the various systems disclosed herein using the processes disclosed herein. While the disclosure may reference to a user hovering over, pointing at, or clicking on a particular item, other techniques may be used to detect an item of user interest. For example, the user may touch the item via a touch screen, or otherwise indicate an interest. The user interfaces described herein may be presented on a user terminal, such as a laptop computer, desktop computer, tablet computer, smart phone, virtual reality headset, augmented reality headset, or other terminal type. The user terminals may be associated with user input devices, such as touch screens, microphones, touch pads, keyboards, mice, styluses, cameras, etc. While the foregoing discussion and figures may illustrate various types of menus, other types of menus may be used. For example, menus may be provided via a drop down menu, a tool bar, a pop up menu, interactive voice response system, or otherwise.

The various features and processes described herein may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "for example," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y or Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y or at least one of Z to each be present.

While certain example embodiments have been described, these embodiments have been presented by way of example only, and are not intended to limit the scope of the disclosure. Thus, nothing in the foregoing description is intended to imply that any particular element, feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

It should be emphasized that many variations and modifications may be made to the described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated herein, it should be noted that the use of particular terminology when describing certain features or aspects of the invention should not be taken to imply that the terminology is being re-defined herein to be restricted to including any specific characteristics of the features or aspects of the invention with which that terminology is associated.

What is claimed is:

1. An application layer protocol running on a user device using one or more hardware processors, the application layer protocol providing decryption and integration of encrypted and disparate portions of medical health data of a patient, the application layer protocol comprising:
    software, that when executed by the one or more hardware processors, causes the software to:
    receives the disparate encrypted portions of medical health data of the patient, wherein the disparate encrypted portions are received via connections between the user device and a plurality of servers which store portions of the medical health data of the patient, and wherein the portions are routed to the user device as encrypted information;
    decrypts the disparate encrypted portions of medical health data and compiles the portions of medical health data into an electronically readable medical record, wherein the decryption and compiling are performed according to one or more constraints defined by a trust relationship between the requestor and the patient, and wherein the constraints comprise one or more of (1) a particular identity of a requestor authorized to access the medical record, (2) one or more user devices authorized to access the medical record, (3) time information specifying a time period during which the medical record can be accessed; and
    provides the medical record for display to a user.

2. The application layer protocol of claim 1, wherein the software executed by the hardware processors comprises a software agent, and wherein the software agent is configured to provide information to front-end applications.

3. The application layer protocol of claim 2, wherein providing the medical record for display comprises:
    providing, to a particular front-end application, the electronically readable medical record; and
    presenting, by the particular front-end application, the medical record for display.

4. The application layer protocol of claim 1, wherein the software:
    monitors satisfaction of the constraints; and
    based on determining that a violation of a constraint, causes presentation of the medical record to be stopped.

5. The application layer protocol of claim 4, wherein a constraint indicates a time during which the medical record can be accessed, and wherein the software:
    identifies that a current time exceeds the indicated time; and
    causes presentation of the medical record to be stopped.

6. The application layer protocol of claim 1, wherein the software:
    receives updates to the medical record;
    encrypts the updates, and provides the encrypted updates to an outside system for storage, the updates being trusted to the requestor.

7. The application layer protocol of claim 1, wherein the user device communicates with the servers via the application layer protocol, and wherein the servers route stored portions of the medical health data of the patient according to the trust relationship between the requestor and the patient.

8. A method of establishing a trusted relationship between a patient and a medical record accessor, the trusted relationship establishing permission for the medical record accessor to access at least a portion of the patient's medical records, the method comprising:
    establishing an identity of the patient based on a plurality of peripheral information about the patient, verification of the identity of the patient by a trusted verifier, or based on biometric information associated with the patient;
    providing a user with a request to establish a trusted relationship with a medical record accessor;
    receiving a request by the medical record accessor to access medical records of the patient; and
    providing the medical record accessor access to the medical records of the patient comprising establishing connection between a requesting device of the medical record accessor and a plurality of servers storing portions of the medical records, wherein the portions of the medical records are routed to the requesting device via the established connections as encrypted information for decryption on the requesting device, and wherein the encrypted information is configured to be decrypted based on satisfaction of one or more constraints comprising (1) a particular identity of a requestor authorized to access the medical records, (2) one or more user devices authorized to access the medical records, (3) time information specifying a time period during which the medical records can be accessed.

9. The method of claim 8, wherein the method further comprises:
generating a unique identifier associated with the patient based on one or more of the plurality of peripheral information; and
associating the unique identifier with the patient, such that the medical records are anonymous.

10. The method of claim 9, wherein the unique identifier is a cryptographic hash of one or more of the plurality of peripheral information.

11. The method of claim 9, wherein the medical records are separated into portions, and wherein the method further comprises:
causing association of the unique identifier with the patient's medical records, such that portions of the medical records do not include personally identifiable information associated with the patient.

12. The method of claim 8, wherein providing a user with a request to establish a trusted relationship with a medical record accessor comprises:
causing activation of an application on a user device of the patient, the application presented a user interface specifying whether trust is to be established.

13. The method of claim 12, wherein the user interface specifies that trust is to be established with a group of medical record accessors that includes the medical record accessor, or wherein the user interface specifies that trust is to be established with the medical record accessor.

14. The method of claim 8, wherein the trusted relationship indicates portions of the patient's medical records that the medical record accessor is authorized to access.

15. The method of claim 8, further comprising:
in response to receiving the request, determining that the medical record accessor has been trusted by the patient; and
providing the medical record accessor access to the medical records.

16. The method of claim 8, wherein the portions of the medical records are routed to the requesting device via an application-layer protocol which enforces the one or more constraints.

17. A method of confirming identity of a patient and providing authorized access to anonymous medical information of the patient, the method comprising:
by a hardware system of one or more computers,
receiving a request, from a requestor's user device, for access to medical information associated with a patient;
causing the request for medical information to be presented on a patient's user device, the request indicating non-unique identifier features of patients that are usable to establish an identify of a specific patient;
in response to receiving responses to the requests, determining that the patient uniquely corresponds to the medical information and generating user account information from the patient, the user account information referencing a unique identifier associated with the medical information, wherein the patient establishes a trust relationship with a requestor associated with the requestor's user device; and
establishing, based on the trust relationship, connections between the requestor's user device and a plurality of servers storing portions of the medical information, wherein the respective portions of the medical information are routed to the requesting device via the established connections as encrypted information on the requestor's user device, and wherein the encrypted information is configured to be decrypted based on satisfaction of one or more constraints comprising (1) a particular identity of a requestor authorized to access the medical information, (2) one or more user devices authorized to access the medical information, (3) time information specifying a time period during which the medical information can be accessed.

18. The method of claim 17, further comprising:
receiving, from the user device of the patient, a request to establish the trust relationship with the requestor, wherein the trust relationship indicates authorization to access the patient's medical information; and
updating one or more databases to indicate the trust.

* * * * *